United States Patent
Montello et al.

(10) Patent No.: US 10,045,799 B2
(45) Date of Patent: Aug. 14, 2018

(54) POSTERIOR VERTEBRAL PLATING SYSTEM

(71) Applicant: DePuy Synthes Products, Inc., Raynham, MA (US)

(72) Inventors: Albert A. Montello, West Chester, PA (US); Hyun W. Bae, Los Angeles, CA (US); William L. Strausbaugh, West Chester, PA (US); Christopher M. Bonner, West Chester, PA (US); William P. McDonough, West Chester, PA (US); David K. Koch, West Chester, PA (US); Jordan N. Milford, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 11 days.

(21) Appl. No.: 15/238,383

(22) Filed: Aug. 16, 2016

(65) Prior Publication Data
US 2016/0354122 A1    Dec. 8, 2016

Related U.S. Application Data

(63) Continuation of application No. 14/491,769, filed on Sep. 19, 2014, now Pat. No. 9,433,443, which is a
(Continued)

(51) Int. Cl.
*A61B 17/80* (2006.01)
*A61B 17/70* (2006.01)
(Continued)

(52) U.S. Cl.
CPC ........ *A61B 17/7059* (2013.01); *A61B 17/701* (2013.01); *A61B 17/7049* (2013.01);
(Continued)

(58) Field of Classification Search
CPC ............ A61B 17/8061; A61B 17/8052; A61B 17/8057; A61B 17/80
(Continued)

(56) References Cited

U.S. PATENT DOCUMENTS

| | | | |
|---|---|---|---|
| 4,957,497 A | 9/1990 | Hoogland et al. | |
| 5,139,498 A | 8/1992 | Astudillo Ley | |

(Continued)

FOREIGN PATENT DOCUMENTS

| | | |
|---|---|---|
| CN | 1154441 | 6/2004 |
| DE | 4343117 | 6/1995 |

(Continued)

OTHER PUBLICATIONS

Sharan, Ashwini D. et al., "MIS Posterior Cervical Spine Surgery: Five-Level Fusion through a Novel Cervical Tube," *JHN Journal* (2011) 6:2, pp. 2-4.

(Continued)

*Primary Examiner* — Ellen C Hammond
*Assistant Examiner* — Christina Negrellirodrigue
(74) *Attorney, Agent, or Firm* — Dunlap Codding, P.C.

(57) ABSTRACT

A posterior vertebral plating system comprising a plate and a plurality of attachment members. The plate has a plurality of holes extending through the plate from an upper surface to a lower surface, and the plate is configured to extend along the posterior side of at least two vertebrae adjacent at least one boney structure of each of the vertebrae. The holes are spaced in such a way that a first plurality of holes is positionable over a boney structure of a first vertebra to define a plurality of fixation points to the first vertebra and a second plurality of holes is positionable over boney structure of a second vertebra to define a plurality of fixation points to the second vertebra. The attachment members are insertable through the holes of the plate and into the boney (Continued)

structure of a corresponding vertebra to fix the plate to the vertebra.

16 Claims, 28 Drawing Sheets

Related U.S. Application Data continuation of application No. 13/437,792, filed on Apr. 2, 2012, now Pat. No. 8,845,697.

(60) Provisional application No. 61/470,821, filed on Apr. 1, 2011.

(51) Int. Cl.
A61B 17/86 (2006.01)
A61B 17/00 (2006.01)

(52) U.S. Cl.
CPC .......... *A61B 17/80* (2013.01); *A61B 17/8057* (2013.01); *A61B 17/8615* (2013.01); *A61B 17/8605* (2013.01); *A61B 2017/00933* (2013.01)

(58) Field of Classification Search
USPC ............................ 606/70, 71, 246, 280–299
See application file for complete search history.

(56) References Cited

U.S. PATENT DOCUMENTS

| | | |
|---|---|---|
| 5,275,601 A | 1/1994 | Gogolewski et al. |
| 5,372,598 A | 12/1994 | Luhr et al. |
| 5,531,746 A | 7/1996 | Errico et al. |
| 5,558,674 A | 9/1996 | Heggeness et al. |
| 5,616,144 A | 4/1997 | Yapp et al. |
| 5,647,872 A | 7/1997 | Gilbert et al. |
| 5,653,708 A | 8/1997 | Howland |
| 5,709,686 A | 1/1998 | Talos et al. |
| 5,718,705 A | 2/1998 | Sammarco |
| 6,093,188 A | 7/2000 | Murray |
| 6,096,040 A | 8/2000 | Esser |
| 6,206,881 B1 | 3/2001 | Frigg et al. |
| 6,217,578 B1 | 4/2001 | Crozet et al. |
| 6,322,562 B1 | 11/2001 | Wolter |
| 6,364,883 B1 | 4/2002 | Santilli |
| 6,592,586 B1 | 7/2003 | Michelson |
| 6,669,700 B1 | 12/2003 | Farris et al. |
| 6,890,335 B2 | 5/2005 | Grabowski et al. |
| 6,955,677 B2 | 10/2005 | Dahners |
| 6,974,461 B1 | 12/2005 | Wolter |
| 7,128,744 B2 | 10/2006 | Weaver et al. |
| 7,166,111 B2 | 1/2007 | Kolb et al. |
| 7,169,150 B2 | 1/2007 | Shipp et al. |
| 7,223,269 B2 | 5/2007 | Chappuis |
| 7,341,587 B2 | 3/2008 | Molz, IV et al. |
| 7,618,441 B2 | 11/2009 | Groiso |
| 7,637,928 B2 | 12/2009 | Fernandez |
| 7,695,500 B2 | 4/2010 | Markworth |
| 7,744,630 B2 | 6/2010 | Lancial |
| 7,776,076 B2 | 8/2010 | Grady, Jr. et al. |
| 7,806,911 B2 | 10/2010 | Peckham |
| 7,901,433 B2 | 3/2011 | Forton et al. |
| 7,942,912 B2 | 5/2011 | Brockmeyer et al. |
| 7,976,570 B2 | 7/2011 | Wagner et al. |
| 8,025,677 B2 | 9/2011 | Freid et al. |
| 8,048,076 B2 | 11/2011 | Michelson |
| 8,070,782 B2 | 12/2011 | McKay |
| 8,088,148 B2 | 1/2012 | Falahee |
| 8,097,021 B1 | 1/2012 | Kornel |
| 8,100,946 B2 | 1/2012 | Strausbaugh et al. |
| 8,105,366 B2 | 1/2012 | Null et al. |
| 8,231,661 B2 | 7/2012 | Carls et al. |
| 8,262,696 B2 | 9/2012 | Falahee |
| 8,282,681 B2 | 10/2012 | McLeod et al. |
| 8,343,194 B2 | 1/2013 | Aflatoon |
| 8,343,196 B2 | 1/2013 | Schneider |
| 8,366,748 B2 | 2/2013 | Kleiner |
| 8,485,413 B2 | 7/2013 | Scheib et al. |
| 8,517,239 B2 | 8/2013 | Scheib et al. |
| 8,623,020 B2 | 1/2014 | Kim et al. |
| 8,623,062 B2 | 1/2014 | Kondrashov |
| 8,696,707 B2 | 4/2014 | Sutterlin, III |
| 8,715,321 B2 | 5/2014 | Butler et al. |
| 8,758,344 B2 | 6/2014 | Michelson |
| 8,870,882 B2 | 10/2014 | Kleiner |
| 8,951,254 B2 | 2/2015 | Mayer et al. |
| 8,974,497 B2 | 3/2015 | Cho et al. |
| 8,986,305 B2 | 3/2015 | Aflatoon et al. |
| 8,992,579 B1 | 3/2015 | Gustine et al. |
| 9,011,491 B2 | 4/2015 | Carl et al. |
| 9,011,492 B2 | 4/2015 | McCormack et al. |
| 9,060,787 B2 | 6/2015 | Blain et al. |
| 9,101,410 B1 | 8/2015 | Urrea |
| 9,179,911 B2 | 11/2015 | Morgan et al. |
| 2003/0055429 A1 | 3/2003 | Ip et al. |
| 2005/0182408 A1 | 8/2005 | Pfefferle et al. |
| 2005/0267480 A1 | 12/2005 | Suddaby |
| 2006/0004363 A1 | 1/2006 | Brockmeyer et al. |
| 2006/0036250 A1 | 2/2006 | Lange et al. |
| 2006/0235397 A1* | 10/2006 | Sanders ............. A61B 17/8061 606/280 |
| 2006/0241597 A1 | 10/2006 | Mitchell et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2007/0260244 A1 | 11/2007 | Wolter |
| 2007/0276367 A1 | 11/2007 | Puno |
| 2008/0033437 A1 | 2/2008 | Shipp et al. |
| 2008/0097448 A1 | 4/2008 | Binder et al. |
| 2008/0132954 A1 | 6/2008 | Sekhon et al. |
| 2008/0140130 A1 | 6/2008 | Chan et al. |
| 2008/0177311 A1 | 7/2008 | Winslow et al. |
| 2008/0183217 A1 | 7/2008 | Glaser |
| 2008/0208263 A1 | 8/2008 | Butler et al. |
| 2008/0228230 A1 | 9/2008 | Ferree |
| 2009/0018557 A1 | 1/2009 | Pisharodi |
| 2009/0076553 A1 | 3/2009 | Wolter |
| 2009/0163920 A1 | 6/2009 | Hochschuler et al. |
| 2009/0163960 A1 | 6/2009 | Binder et al. |
| 2009/0192549 A1 | 7/2009 | Sanders et al. |
| 2009/0248082 A1 | 10/2009 | Crook et al. |
| 2009/0281543 A1 | 11/2009 | Orbay et al. |
| 2009/0306667 A1 | 12/2009 | Lee et al. |
| 2010/0082067 A1 | 4/2010 | Kondrashov |
| 2010/0131013 A1 | 5/2010 | Ralph et al. |
| 2010/0137919 A1 | 6/2010 | Wolter |
| 2010/0145386 A1 | 6/2010 | Greenhalgh et al. |
| 2010/0160966 A1 | 6/2010 | Melkent |
| 2010/0193566 A1 | 8/2010 | Scheib et al. |
| 2010/0211109 A1 | 8/2010 | Doerr |
| 2011/0004252 A1* | 1/2011 | Velikov ............... A61B 17/80 606/280 |
| 2011/0015681 A1 | 1/2011 | Elsbury |
| 2011/0202092 A1 | 8/2011 | Frigg et al. |
| 2011/0230971 A1 | 9/2011 | Donner et al. |
| 2011/0295325 A1 | 12/2011 | Wagner et al. |
| 2012/0016365 A1 | 1/2012 | Freid et al. |
| 2012/0022600 A1 | 1/2012 | Overes et al. |
| 2012/0283776 A1 | 11/2012 | Mishra |
| 2013/0123923 A1 | 5/2013 | Pavlov et al. |
| 2014/0207191 A1 | 7/2014 | Kornel |
| 2014/0276807 A1 | 9/2014 | Lovell |
| 2014/0277141 A1 | 9/2014 | Baynham |
| 2014/0277142 A1 | 9/2014 | Blain et al. |
| 2015/0173746 A1 | 6/2015 | Baxter, III et al. |
| 2015/0190175 A1 | 7/2015 | Oldakowski et al. |
| 2015/0209089 A1 | 7/2015 | Chataigner et al. |
| 2015/0215259 A1 | 7/2015 | Pellicer et al. |
| 2015/0272573 A1 | 10/2015 | Euteneuer et al. |
| 2015/0297229 A1 | 10/2015 | Schellin et al. |

(56) References Cited

U.S. PATENT DOCUMENTS

2015/0297230 A1   10/2015   Schellin et al.
2015/0297231 A1   10/2015   Huitema et al.
2015/0297233 A1   10/2015   Huitema et al.

FOREIGN PATENT DOCUMENTS

| DE | 19858889 | 6/2000 |
|---|---|---|
| DE | 10140442 | 3/2003 |
| DE | 102006060933 | 10/2008 |
| EP | 1143867 | 11/1999 |
| EP | 1211993 | 9/2000 |
| EP | 1211994 | 9/2000 |
| EP | 2120754 | 11/2009 |
| EP | 2394587 | 7/2015 |
| EP | 2713897 | 8/2015 |
| FR | 2386301 | 4/1977 |
| FR | 2531855 | 6/1983 |
| JP | 2008206143 | 9/2008 |
| JP | 2009511918 | 3/2009 |
| JP | 2010536427 | 12/2010 |
| RU | 2196535 RU | 1/2003 |
| RU | 2234878 | 8/2004 |
| UZ | 292 | 6/2007 |
| WO | 95/16403 | 6/1995 |
| WO | 1999/38448 | 8/1999 |
| WO | 2001/19264 | 3/2001 |
| WO | 2001/19268 | 3/2001 |
| WO | 2005/018472 | 3/2005 |
| WO | 2007/044954 | 4/2007 |
| WO | 2008/077491 | 7/2008 |
| WO | 2009/023666 | 2/2009 |
| WO | 2011/003494 | 1/2011 |
| WO | 2012/135860 | 10/2012 |

OTHER PUBLICATIONS

International Search Report and Written Opinion (PCT/US2012/031901); dated Jan. 17, 2013.
Extended European Search Report (European Patent Application No. 15162416.0); dated Aug. 14, 2015.
Notification of Reasons for Refusal (Japanese Patent Application No. 2014-502700); dated Feb. 9, 2016.
Decision on Grant Patent for Invention (RU 2013148808); dated Oct. 27, 2016.
Extended European Search Report (EP17168305.5); dated Sep. 7, 2017.
Notification of Reasons for Refusal (Japanese Patent Application No. 2016-244158); dated Sep. 5, 2017.
Extended European Search Report (European Patent Application No. 18160551.0); dated Jun. 28, 2018.

\* cited by examiner

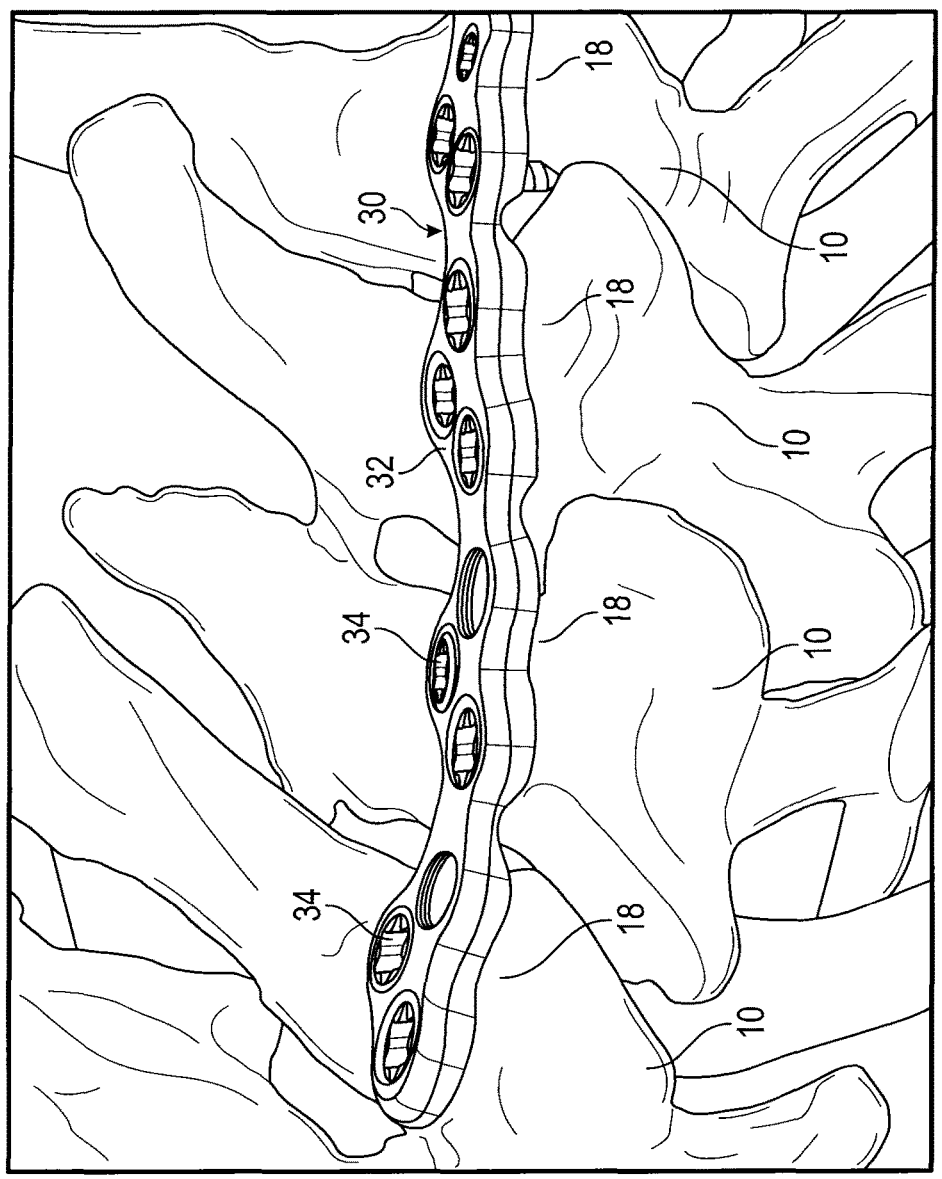

POSTERIOR VERTEBRAL PLATING SYSTEM

CROSS-REFERENCE TO RELATED APPLICATIONS

This application is a continuation of U.S. application Ser. No. 14/491,769, filed Sep. 19, 2014, which is a continuation of U.S. application Ser. No. 13/437,792, filed Apr. 2, 2012, now U.S. Pat. No. 8,845,697, which claims priority to U.S. Provisional Application Ser. No. 61/470,821, filed Apr. 1, 2011, the entirety of each of which being hereby expressly incorporated herein by reference.

BACKGROUND

The spinal column of bones is highly complex in that it includes over twenty bones coupled to one another so as to house and protect critical elements of the nervous system. In addition, the spine is a highly flexible structure, capable of a high degree of curvature and twist in multiple directions. The most flexible of all the regions of the spinal column is the cervical spine.

The bones and connective tissue of an adult human spinal column are coupled sequentially to one another by a tri-joint complex which consists of an anterior disc and the two posterior facet joints. The anterior discs of adjacent bones are separated and cushioned by cartilage spacers referred to as intervertebral discs. The vertebral bones of the spine are classified as cervical, thoracic, lumbar, and sacral. The cervical portion of the spine, which comprises the upper portion of the spine up to the base of the skull, includes the first seven vertebrae. The twelve intermediate bones comprise the thoracic vertebrae, and connect to the lower spine which comprises the five lumbar vertebrae. The base of the spine is the sacral bones (including the coccyx). The vertebrae which make up the cervical portion of the spine are generally smaller than those of the thoracic and lumbar spine.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determines the appropriate surgical protocol and implantation assembly. The use of posterior plates for stabilization and immobilization of the cervical spine is known. A posterior plate is a narrow elongated plate having a series of spaced holes through which screws may be inserted to fix the plate to the vertebrae. A pair of posterior plates is placed across the lateral posterior surfaces of a set of sequential cervical bones and is secured to the bone by using one screw per vertebra, thereby preventing the bones from moving relative to one another in either the vertical or horizontal planes.

Because the spine is routinely subject to high compression and torsional loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for screws which are inserted into the bone at an angle with respect to the plate, the amount of bone which must fail increases substantially as compared with screws which are implanted perpendicularly with respect to the plate.

An additional concern with screws being implanted in the posterior side of the cervical spine is that there are sensitive and important structures adjacent to the boney structures, such as the lateral masses and the laminae, which, because of their proximity to the implant, may be damaged by insertion or dislocation of screws. In the cervical spine, the vertebral arteries are disposed medially beneath the lateral masses or lamina and comprise critical structures which cannot be compromised. In addition, the facet joints which provide natural coupling of sequential bones together must also be avoided it possible. Avoidance of these bodies has been a critical and ongoing concern with respect to posterior screw insertion. Posterior plates of the prior art have provided little in the way of reasonable or practical solutions for ensuring proper screw insertion.

Posterior screw plate assemblies necessarily include a plurality of screws which are inserted through a single plate. However, if a single screw loosens with respect to the surrounding bone into which it has been inserted, loss of fixation occurs and possible neurological repercussions may result.

One way to avoid the drawbacks of current plate systems has been to use fixation systems that employ polyaxial screws, rods, and hooks. However, while polyaxial screws provide a surgeon with the ability to locate the screws in optimum locations, the ability to do so requires a high degree of skill and experience. Further, to ensure proper placement of polyaxial screws, surgeons typically utilize fluoroscopy for an extended period of time which can expose patients to unwanted radiation.

BRIEF DESCRIPTION OF THE DRAWINGS

FIG. 7B is a lateral, elevational view of one of the bone plates shown connected to the posterior side of the plurality of vertebra.

DETAILED DESCRIPTION OF EXEMPLARY EMBODIMENTS

Figure 1A:
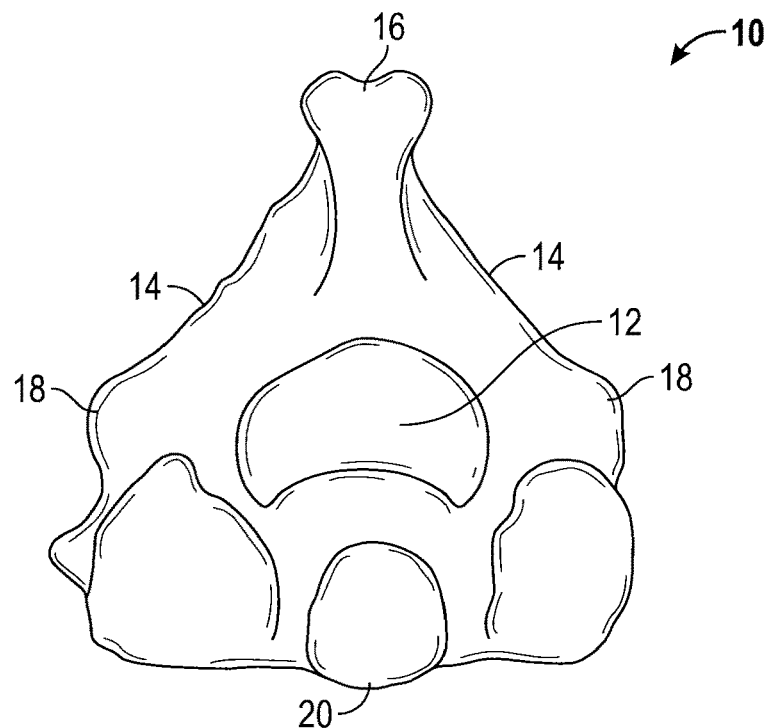
FIG. 1A is a diagrammatic top view of a cervical vertebra.

Before explaining at least one embodiment of the presently disclosed inventive concepts in detail, it is to be understood that the presently disclosed inventive concepts are not limited in their application to the details of construction, experiments, exemplary data, and/or the arrangement of the components as set forth in the following description or illustrated in the drawings. The presently disclosed inventive concepts are capable of other embodiments or of being practiced or carried out in various ways. Also, it is to be understood that the phraseology and terminology employed herein is for purpose of description and convenience and should not be regarded as limiting.

Figure 1B:
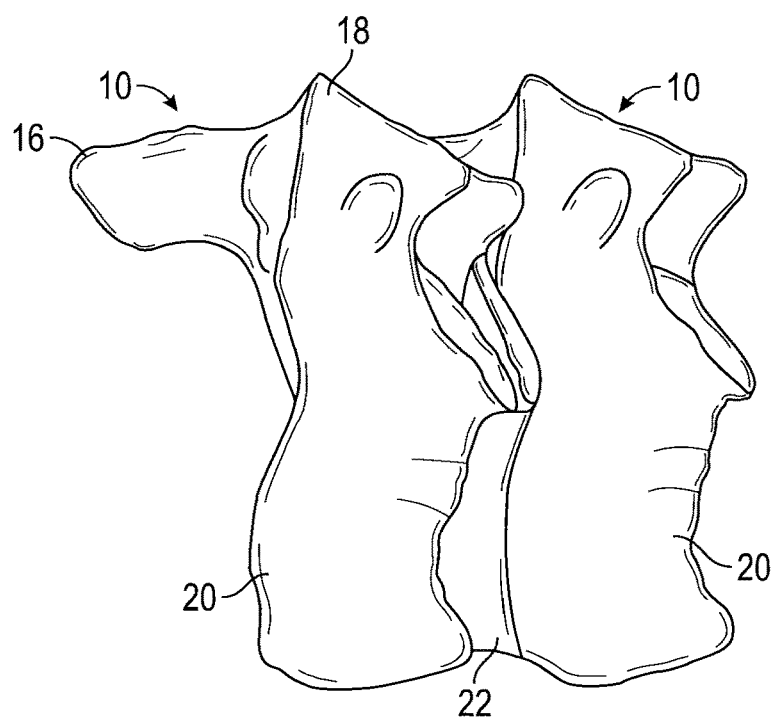
FIG. 1B is a diagrammatic side view of two sequentially aligned cervical vertebrae.
Figure 2:
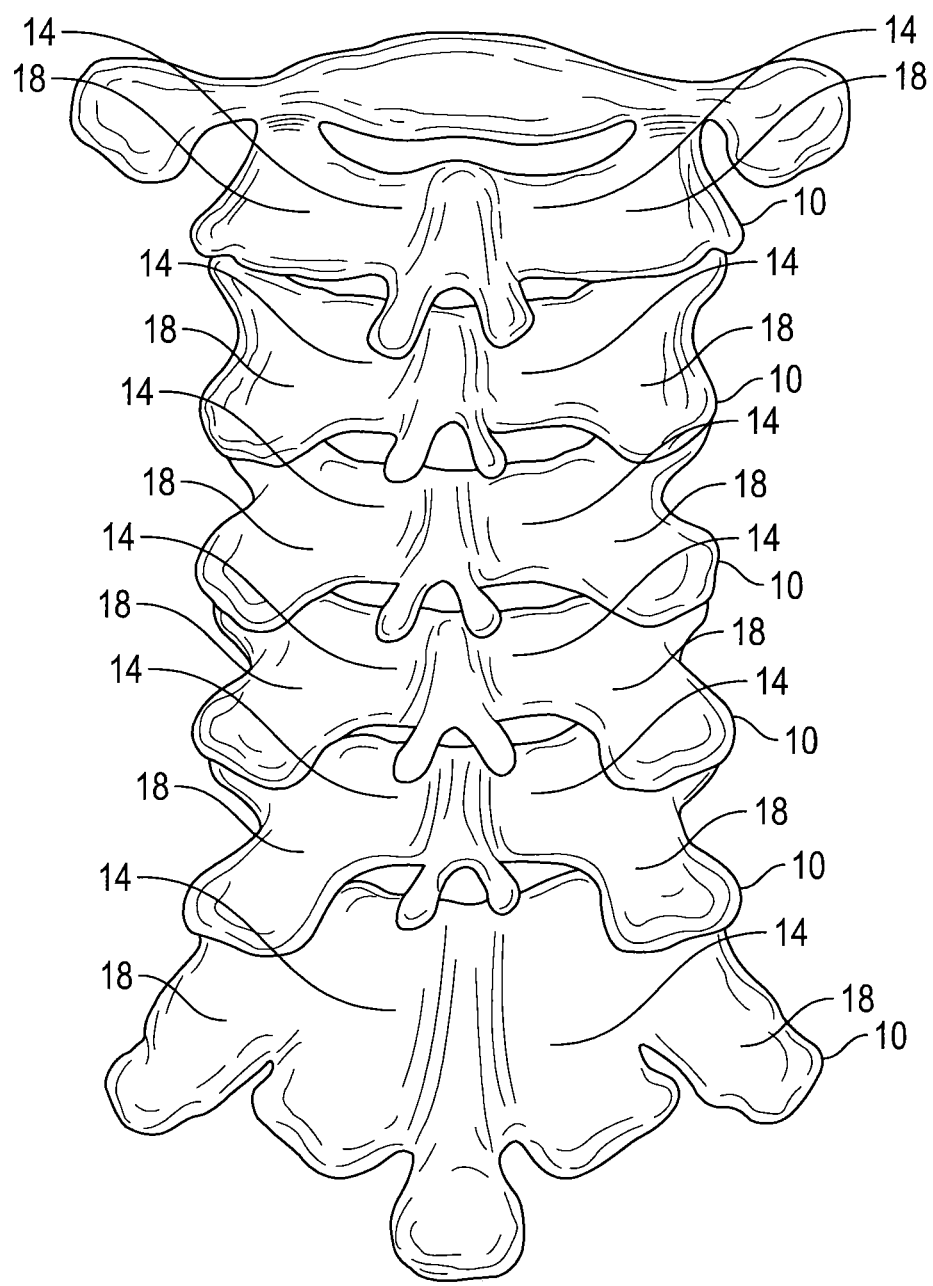
FIG. 2 is a diagrammatic posterior view of the cervical portion of the spine illustrating the lateral masses and lamina of the cervical vertebrae.

Referring now to the drawings, and more particularly to FIGS. 1A, 1B, and 2, a typical cervical vertebra 10 is shown in a superior view in FIG. 1A; two adjacent cervical vertebrae 10 are shown in a lateral view in FIG. 1B; and the cervical vertebrae are shown from a posterior view in FIG. 2. The spinal cord (not shown) is housed within a central canal 12 that runs the length of the spinal column and is protected along the posterior side of the spinal column by a bony arch, or roof, made up of a pair of lamina 14 and a rearward (dorsally) and downwardly extending portion called the spinous process 16 located between the two laminae 14. Two laterally extending bulk structures, one on either side of each lamina 14, define the two lateral masses 18. The portions of the vertebrae 10 which define the anterior portion of the spine comprise cylindrically shaped bone portions which are stacked one on top of the other. These portions of the vertebrae 10 are referred to as vertebral bodies 20 and are separated from each other by intervertebral discs 22 which provide a cushioning effect between the vertebrae 10. The lateral masses 18 comprise a pair of bone bridges which couple the anterior vertebral body 20 to the laminae 14 of the same vertebra 10

Referring now to FIGS. 3-7B, a posterior vertebral plating system 30 constructed in accordance with the inventive concepts disclosed herein is shown. Although intended for use primarily in the cervical portion of the spine, it should be understood that the posterior vertebral plating system 10 may be used on any boney structure of the spine, including lumbar, thoracic, and sacral, and the plating system 10 can be used in any direction, e.g., posterior, anterior, or lateral.

The posterior vertebral plating system 30 includes a bone plate 32 and a plurality of attachment members 34. As used herein, the term "attachment member" is intended to refer to any member that may be used to attach a bone plate to a vertebral bone surface, including, but not limited to, screws, clamps, wire, compression screws, locking screws, tacks, pins, nails, studs, rivets, fasteners, or other such devices known to persons having ordinary skill in the art.

The bone plate 32 is intended to stabilize multiple vertebrae. To this end, the bone plate 32 has a length dimensioned to extend along the posterior side of at least two vertebrae. It will be appreciated that the length of the bone plate 32 may be varied depending on the number of vertebrae to be stabilized. Because the bone plate 32 is intended to be fixed to boney structures of the posterior side of vertebrae (e.g., lateral mass, lamina), the plate 32 has a width and shape that allows the bone plate 32 to be positioned over the boney structures of the posterior side of adjacent vertebrae. In one embodiment, the bone plate 32 may have an overall width in a range from about 8 mm to about 14 mm, but more desirably, less than about 12 mm. The width of the bone plate 32 may be varied or curved or contoured along one side such that the bone plate 32 is configured to have a plurality of nodes 36 which define recesses 38 between each of the nodes 36 to reduce the outer contour and size of the bone plate 32. To this end, the bone plate 32 may have at least one minor width 40 at a most narrow portion and at least one major width 42 at a widest portion. In one embodiment, the minor width 40 may be approximately 5 mm and the major width 42 in a range of approximately 9 mm to 12 mm. The reduced width portion between each of the nodes 36 provides an area of reduced material for bending of the bone plate 32 as may be required by the spinal anatomy, as well as provides for better visualization of the boney surface below the bone plate 32. The bone plate 32 has a thickness 44, which may be in a range including, but not limited to, about 1 mm to about 4 mm, for example.

The bone plate 32 has an upper surface 46 and a lower surface 48. The bone plate 32 can include a rounded upper edge 50 to reduce irritation of surrounding tissue. The rounded upper edge 50 reduces the amount of trauma or irritation that would be experienced by the surrounding soft tissue. The lower surface 48 of the bone plate 32 may be configured to conform to the contour of the vertebral bodies at each of the instrumented levels of the spine. In some embodiments, the lower surface 48 can be provided with a textured surface 52 (FIG. 4B) which may include a variety of geometric shapes and/or protrusions, such as spikes, or other features, such as ridges, posts, pockets, or be treated such as bead blasted or acid etched to enhance its grip on the vertebral body. The bone plate 32 may also have a longitudinal and/or transverse curvature to match the corresponding attachment surface (e.g., the curve of the spine).

Figure 4A:
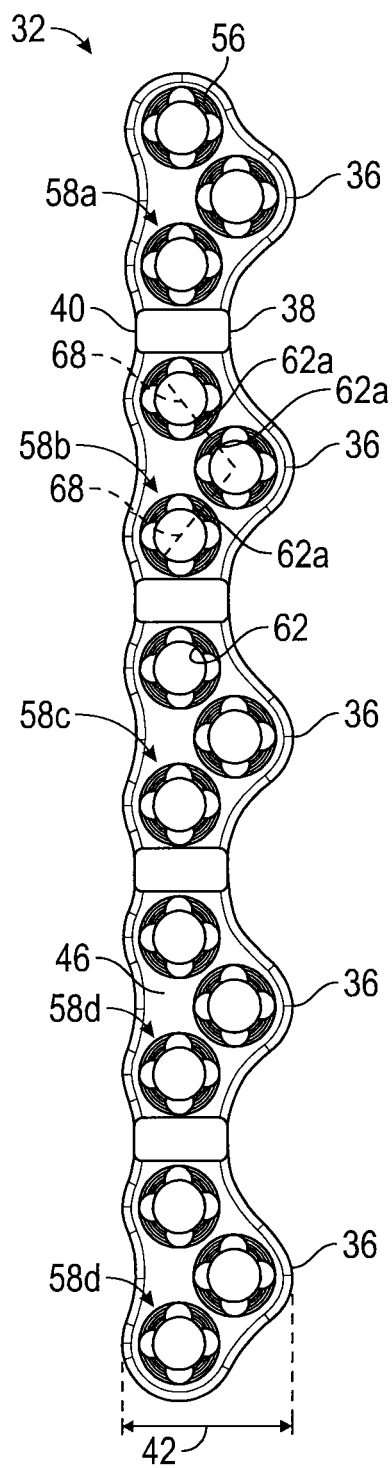
FIG. 4A is a top plan view of a bone plate of the plating system of FIG. 3.
Figure 4B:
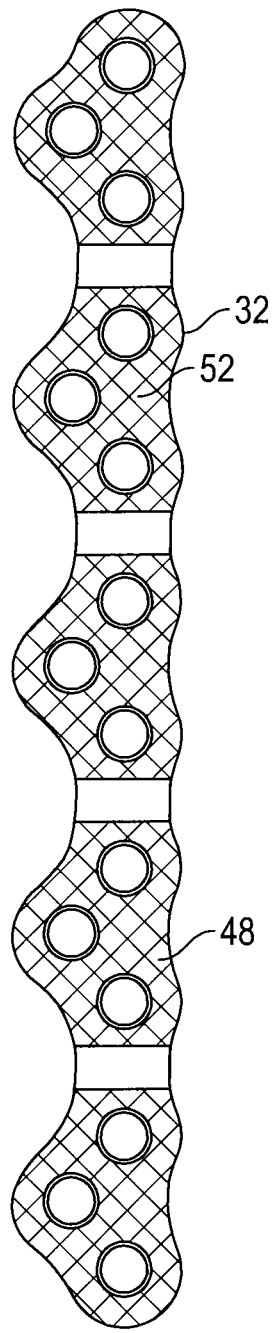
FIG. 4B is a bottom plan view of the bone plate of FIG. 3.

The bone plate 32 has a plurality of holes 56 which extend through the bone plate 32 from the upper surface 46 through the lower surface 48. The holes 56 are dimensioned and arranged relative to one another so that more than one of the holes 56 is positionable or alignable over the posterior boney structures, such as the lateral mass or lamina, of each vertebra to define a plurality of fixation points per vertebra. The holes 56 may be arranged in a variety of ways to provide multiple points of fixation while maintaining the structural strength and rigidity of the bone plate 32. FIGS. 4A and 4B illustrate one exemplary embodiment of a hole pattern where the holes 56 are arranged in a plurality of groups of holes 58a-58e (corresponding with one of the nodes 36) in such a way that at least two to three of the holes 56 is positionable over a single vertebra to define a plurality of fixation points per vertebra. The holes 56 are shown to be arranged in groups of three holes 58a-58e with the holes 56 in each group being arranged in a triangular pattern. In one version, the holes 56 may be arranged in at least two longitudinal rows of holes 56 along the length of the bone plate 32 with the holes 56 of one longitudinal row of holes being staggered and nested relative to the holes 56 of the other longitudinal row of holes 56.

Each group of three holes 58a-58e of holes 56 may be arranged where each laterally adjacent pair of holes is spaced substantially an equal distance and each laterally adjacent pair of holes angled relative to one another in a range from about 30 degrees to about 50 degrees relative to the longitudinal axis of the bone plate 32 so as to result in an overlap of laterally adjacent holes 56 along a longitudinal axis of not more than about 20% (e.g., approximately 10%) of the area of the holes 56 so as to permit longitudinally adjacent holes 56 to remain spaced to align with the lateral mass of the vertebra. Accordingly, it should be apparent that each pair of longitudinally adjacent holes is spaced a greater distance than the laterally adjacent holes. By way of example, the holes 56 may have a diameter to accommodate a screw having an outer diameter in a range from about 1.5 mm to about 3.0 mm (e.g., approximately 2.7 mm), each laterally adjacent pair of holes may be spaced a lateral distance (center to center) in a range from about 2.0 mm to about 4.0 mm (e.g., approximately 2.9 mm) and a longitudinal distance (center to center) in a range of from about 3.0 mm to about 5.0 mm (e.g., approximately 3.5 mm), and each longitudinally adjacent pair of holes may be spaced a longitudinal distance (center to center) in a range from about 6.0 mm to about 8.0 mm (e.g., approximately 7.0 mm) resulting in a bone plate with a width less than 10 mm and a three hole pattern that provides a ratio of hole area/plate area (footprint) in a range of from about 40% to about 60% (e.g., approximately 47%).

The bone plate 32 depicted in FIGS. 6A and 6B includes five nodes and five groupings of holes, and the bone plate 32 has a length so that the bone plate 32 can be engaged to five cervical vertebrae of the spine. However, the bone plate 32 can be configured to fix any number of vertebrae depending upon the length of the bone plate 32 and the number and arrangement of attachment members.

Figure 6:
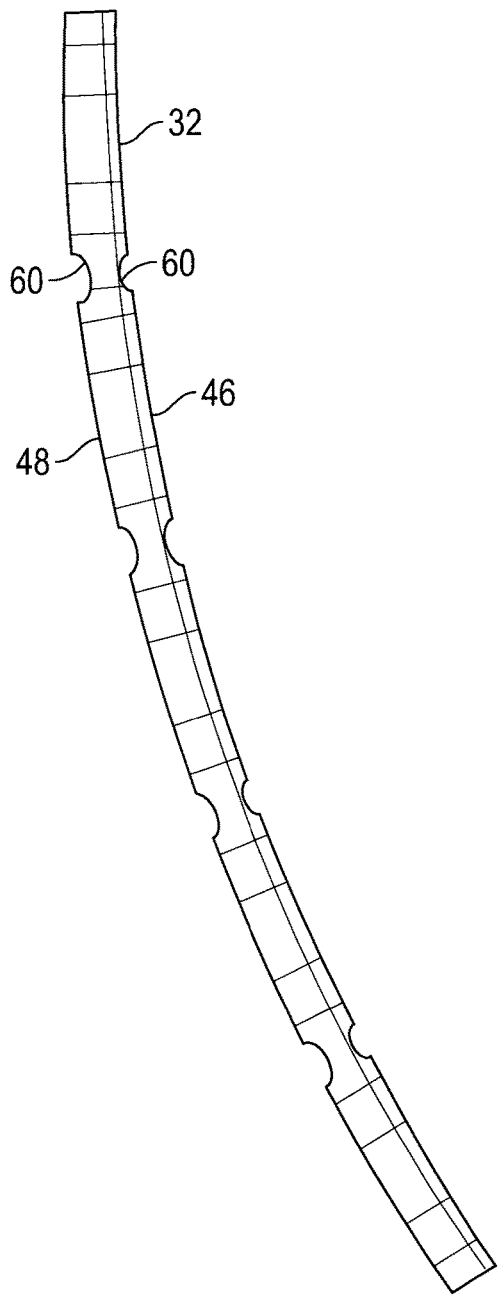
FIG. 6 is a side elevational view of the bone plate of FIG. 3 shown in a curved condition.

In one exemplary version of the bone plate 32, each group of holes 58a-58e is spaced apart from the adjacent group of holes a distance which is generally greater than the distance between laterally adjacent holes 56. Such an arrangement facilitates bending or curving the bone plate 32 to a desired configuration, such as illustrated in FIG. 6, by way of example. To aid in bending the bone plate 32, the bone plate may be provided with transverse grooves 60 in one of the upper surface 46 and the lower surface 48, or both the upper surface 46 and the lower surface 48.

The holes 56 may be formed entirely perpendicular to the plane of the bone plate 32, or may be offset in the general direction which screw angulation is desired to aid in minimizing the risk of comprising vascular and neural structures. For example, the holes 56 may be laterally outwardly angled, e.g., at an angle of approximately 10 to 30 degrees of lateral outward angulation.

Figure 3:
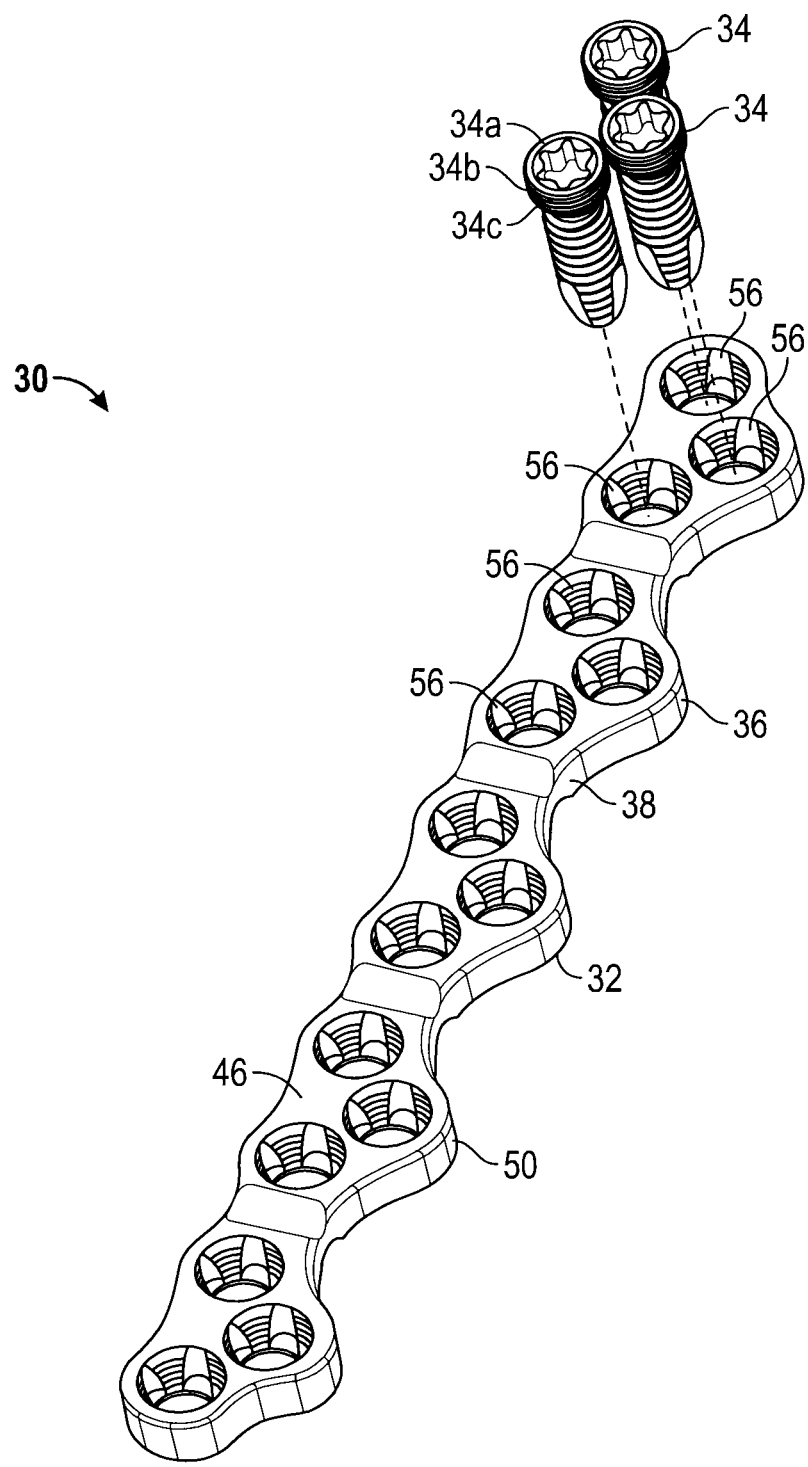
FIG. 3 is a perspective view of a posterior vertebral plating system constructed in accordance with the inventive concepts disclosed herein.
Figure 5A:
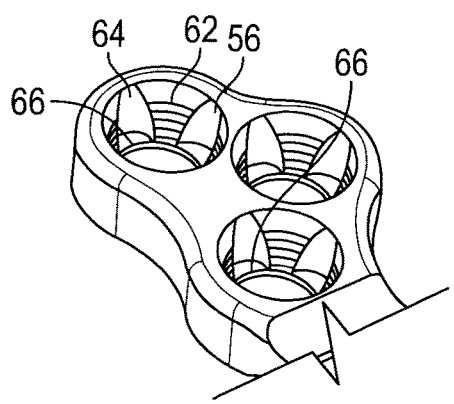
FIG. 5A is an enlarged, perspective view of a portion of the bone plate of FIG. 3.
Figure 5B:
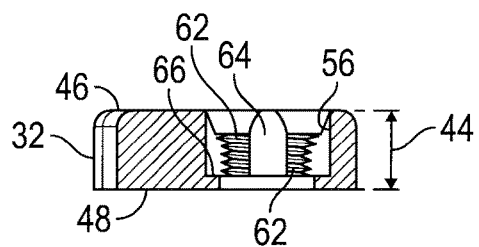
FIG. 5B is cross-sectional view taken along line 5B-5B of FIG. 5A.

Referring to FIGS. 4A, 5A and 5B, each hole 56 is shown to be threaded to receive one of the attachment members 34. Those skilled in the art will understand that any thread configuration may be used, or the holes 56 may even be smooth or non-threaded. In FIGS. 4A, 5A and 5B, each hole 56 is illustrated as being threaded to receive an attachment member 34 in the form of a variable angle locking screw 34a. The holes 56 have a plurality of columns of threads 62 spaced apart to define a plurality of non-threaded recesses 64. In the embodiment illustrated herein, each of the holes 56 has four columns of threads 62. The columns of threads 62 are arranged around the inner surface of each of the holes 56 for engaging threads on a head of locking and variable-angle locking bone screws. Conventional locking screws engage the bone plate 32 coaxially with the central axis of the hole of the bone plate 32. Variable-angle locking screws can engage the bone plate 32 at a selected angle within a range of selectable angles relative to the central axis of hole of the bone plate 32. An example of a variable angle locking screw 34a is illustrated in FIG. 3. The variable-angle locking screw 34a has a head 34b which is at least partially spherical and a thread 34c which has a profile that follows the arc-shaped radius of curvature of the spherical portion of the head 34b. Variable angle locking screws are well known in the art such as disclosed in U.S. 2008/0140130 filed by Chan et al., for example, which is hereby expressly incorporated herein by reference.

During implantation, the variable angle capability of the variable angle locking screw 34a allows a surgeon to place the variable angle locking screw 34a within the vertebra at any angle within defined angulation limits. Thus, the variable angle locking screw 34a provides greater flexibility than does a fixed angle screw.

As best shown in FIGS. 5A and 5B, the holes 56 may be provided with a flange 66 extending between adjacent columns of threads 62 hole near the lower surface 48 of the bone plate 32 in such a way that the flange 66 functions to obstruct the attachment member 34, such as the variable angle screw 34a, from being driven too deeply into the vertebra and thereby limit the risk of injury to patients. In one embodiment, the flanges 66 are formed coextensively with respect to the lower most thread of the columns of threads 62 so as to engage with the threads 34c of the head 43b of the variable angle locking screw 34a upon the head 34b of the variable angle locking screw 34a being fully driven into the hole 56 and thereby provide an obstruction to the variable angle locking screw 34a. It should be appreciated that the attachment member 34 may alternatively, or in addition to, have a flange element or stop member that contacts a portion of the bone plate 32 to limit the depth or distance which the attachment element 34 may be inserted into the bone.

Due to the relatively narrow width of the bone plate 32 and the inclusion of multiple groups of holes, the holes 56 are necessarily positioned relatively close to one another. As such, the strength of the bone plate 32 can be compromised along the narrowest portions of the bone plate 32. As described above, one of those narrow portions is generally located between laterally adjacent holes 56. To increase the strength in these areas, at least one of the columns of threads 62a of one of the holes 56 of a pair of laterally adjacent holes intersects a line 68 (FIG. 4A) extending between the axes of the holes 56 of the pair of laterally adjacent holes 56. Moreover, in certain arrangements, such as shown in FIG. 4A, one of the columns of threads 62a of each of the holes 56 of a pair of laterally adjacent holes intersects and is aligned with the line 68 extending between the axes of the holes 56 of the pair of laterally adjacent holes 56, such that the columns of threads 62 function to provide a thicker area between two laterally adjacent holes than would exist if the non-threaded recesses 64 were aligned. The thicker area provides the advantage of increased strength of the bone plate 32.

Figure 7A:
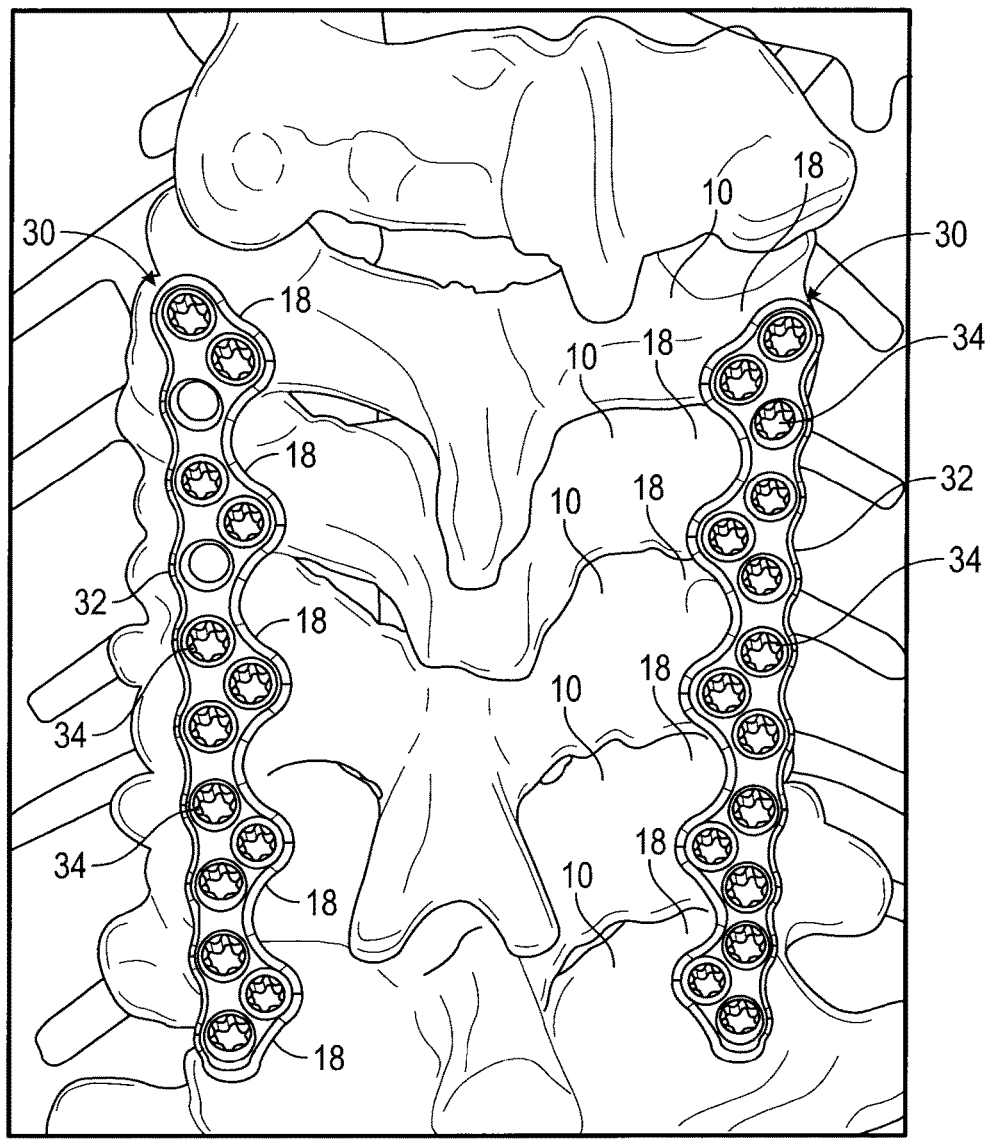
FIG. 7A is a posterior, perspective view of a pair of the bone plates of FIG. 3 shown connected to the posterior side of a plurality of vertebra.

Referring now to FIGS. 7A and 7B, the posterior spinal fixation system 30 is illustrated as being connected to the posterior side of a plurality of vertebrae 10 with the bone plates 32 extending along the posterior side of five vertebrae 10 adjacent the lateral masses 18 of each of the vertebra 10 and the holes 56 being spaced in such a way that a plurality of holes 56 is positioned over the lateral mass 18 of each of the vertebra 10 to define a plurality of fixation points to each of vertebra 10. The attachment members 34 are inserted through selected holes 56 and into the lateral mass 18 of a corresponding vertebra 10 to fix the bone plate 32 to the vertebrae 10. It will be appreciated that the user can elect not to insert an attachment member 34 into selected holes.

Referring now to FIGS. 8-11, another embodiment of a bone plate 32a is illustrated. The bone plate 32a is similar structure and function to the bone plate 32 described above. The bone plate 32a is intended to stabilize multiple vertebrae. To this end, the bone plate 32a has a length dimensioned to extend along the posterior side of at least two vertebrae. It will be appreciated that the length of the bone plate 32a may be varied depending on the number of vertebrae to be stabilized. Because the bone plate 32a is intended to be fixed to boney structures of the posterior side of vertebrae (e.g., lateral mass, lamina), the bone plate 32a has a width and shape that allows the bone plate 32a to be positioned over the boney structures of the posterior side of adjacent vertebrae. In one embodiment, the bone plate 32a may have a width less than about 15 mm, but more desirably, less than about 12 mm.

The bone plate 32a has an upper surface 70 and a lower surface 72. The bone plate 32 can include a rounded upper edge 74 to reduce irritation of surrounding tissue. The rounded upper edge 74 reduces the amount of trauma or irritation that would be experienced by the surrounding soft tissue. The lower surface 72 of the bone plate 32a may be configured to conform to the contour of the vertebral bodies at each of the instrumented levels of the spine. In some embodiments, the lower surface 48 can be provided with a textured surface such that described above in reference to FIG. 4B which may include a variety of geometric shapes and/or protrusions, such as spikes, or other features, such as ridges, posts, pockets, or be treated such as bead blasted or acid etched to enhance its grip on the vertebral body. The bone plate 32a may also have a longitudinal and/or transverse curvature to match the corresponding attachment surface (e.g., the curve of the spine).

The bone plate 32a has a plurality of holes 76 which extend through the bone plate 32a from the upper surface 70 through the lower surface 72. The holes 76 may be entirely perpendicular to the plane of the bone plate 32a, or may be offset in the general direction which screw angulation is desired. For example, the holes 76 may be laterally outwardly angled, e.g., at an angle of approximately 10 to 30 degrees of lateral outward angulation.

Figure 8:
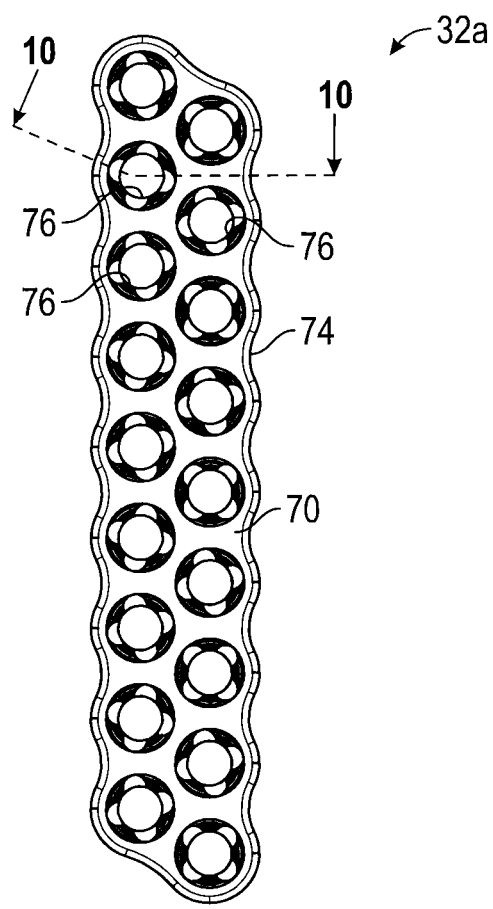
FIG. 8 is a top plan view of another embodiment of a bone plate constructed in accordance with the inventive concepts disclosed herein.
Figure 9:
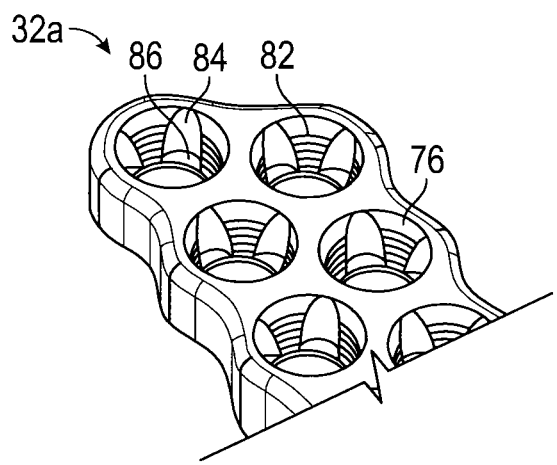
FIG. 9 is a partially cutaway, perspective view of the bone plate of FIG. 8.
Figures 11A, 11B:
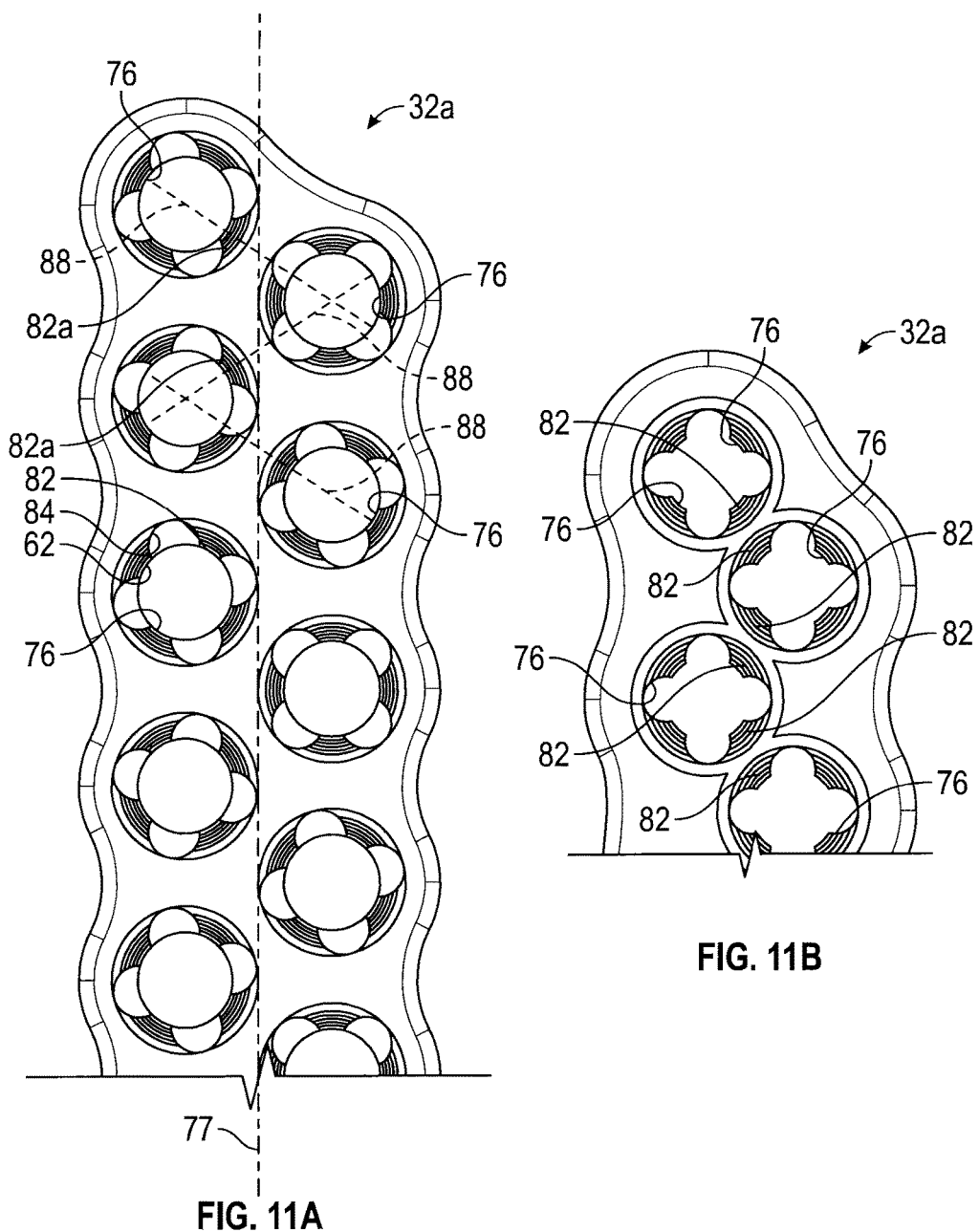
FIG. 11A is a partially cutaway, top plan view of the bone plate of FIG. 8.
FIG. 11B is a partially cutaway, top plan view of another embodiment of a bone plate constructed in accordance with the inventive concepts disclosed herein.

The holes 76 are dimensioned and arranged relative to one another so that more than one of the holes 76 is positionable or alignable over the boney structure, such as a lateral mass or lamina, of each vertebra to define a plurality of fixation points per vertebra. The holes 76 may be arranged in a variety of ways to provide multiple points of fixation while maintaining the structural strength and rigidity of the bone plate 32a. FIGS. 8, 9, and 11A illustrate one embodiment of a hole pattern where the holes 76 are arranged in two longitudinal rows of holes 76 along the length of the bone plate 32a with the holes 76 of one longitudinal row of holes being staggered relative to the holes 76 of the other longitudinal row of holes 76. Each of the holes 76 may be arranged where each laterally adjacent pair of holes 76 are spaced substantially a first distance, and each pair of longitudinally adjacent holes are spaced substantially a second distance where the second distance is greater than the first distance and each laterally adjacent pair of holes are angled relative to one another in a range from about 45 degrees to about 65 degrees (e.g., approximately 57 degrees) relative to the longitudinal axis of the bone plate 32a.

To increase the number of holes per unit length, the holes 76, while shown as being staggered, are not overlapped with one another along a longitudinal axis. However, an innermost point of each of the holes 76 may be aligned with a longitudinal axis 77 to minimize the width of the plate. By way of example, the holes 56 may have a diameter to accommodate a screw having an outer diameter in a range from about 1.5 mm to about 3.0 mm. (e.g., approximately 2.7), each laterally adjacent pair of holes may be spaced a lateral distance in a range from about 3.0 mm to about 5.0 mm (e.g., approximately 4.2 mm) and a longitudinal distance in a range of from about 2.0 mm to about 5.0 mm (e.g., approximately 2.8 mm), and each longitudinally adjacent pair of holes may be spaced a longitudinal distance in a range from about 4.0 mm to about 7.0 mm (e.g., approximately 5.5 mm) resulting in a bone plate with a width less than 12 mm and a four hole pattern providing a ratio of hole area/plate area (footprint) in a range of from about 40% to about 60% (e.g., approximately 49%).

The bone plate 32a can be configured to fix several vertebrae depending upon the size/length of the bone plate 32a and the number and arrangement of attachment members. For example, the bone plate 32a depicted in FIG. 8 includes nine holes 76 in each longitudinal row, and the bone plate 32a has a length so that the bone plate 32a can be attached to five cervical vertebrae of the spine.

Figure 10:
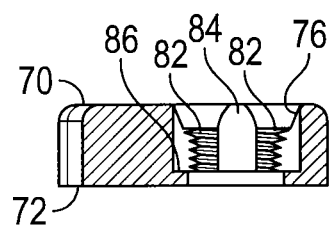
FIG. 10 is a cross-sectional view taken along line 10-10 of FIG. 9.

Like the holes 56 described above, the hole 76 are shown to be threaded to receive one of the attachment members 34. Those skilled in the art will understand that any thread configuration may be used, or the holes 76 may even be non-threaded or smooth. As best shown in FIGS. 9 and 10, each of the holes 56 is illustrated as being threaded to receive an attachment member 34 in the form of a variable angle locking screw 34a (FIG. 3). The holes 76 have a plurality of columns of threads 82 spaced apart to define a plurality of non-threaded recesses 84. In the embodiment illustrated herein, each of the holes 76 has four columns of threads 82. The columns of threads 82 are arranged around the inner surface of each of the holes 76 for engaging threads on a head of locking and variable-angle locking bone screws. Conventional locking screws engage the bone plate 32a coaxially with the central axis of the hole of the bone plate 32a. Variable-angle locking screws can engage the bone plate 32a at a selected angle within a range of selectable angles relative to the central axis of hole of the bone plate 32a.

As best shown in FIGS. 9 and 10, the holes 56 may be provided with a flange 86 extending between adjacent columns of threads 82 hole near the lower surface 72 of the bone plate 32a in such a way that the flange 86 functions to obstruct the attachment member 34, such as the variable angle screw 34a, from being driven too deeply into the vertebra and thereby limit the risk of injury to patients. In one embodiment, the flanges 86 are formed coextensively with respect to the lower most tooth of the columns of threads 82 so as to engage with the threads 34c of the head 43b of the variable angle locking screw 34a upon the head 34b of the variable angle locking screw 34a being fully driven into the hole 76 and thereby provide an obstruction to the variable angle locking screw 34a.

Due to the relatively narrow width of the bone plate 32a and the inclusion of multiple holes, the holes 76 are necessarily positioned relatively close to one another. As such, the strength of the bone plate 32a can be compromised along the narrowest portions of the bone plate 32a. As described above, one of those narrow portions is generally located between laterally adjacent holes 76. To increase the strength in these areas, at least one of the columns of threads 82a of one of the holes 76 of a pair of laterally adjacent holes intersects a line 88 (FIG. 11A) extending between the axes of the holes 76 of the pair of laterally adjacent holes 76 such that the columns of threads 62 function to provide a thicker area between two laterally adjacent holes than would exist if the non-threaded recesses 84 were aligned. The thicker area provides the advantage of increased strength of the bone plate 32a.

FIG. 11B illustrates a modified version of the bone plate 32a illustrating the holes 76 arranged in such a manner that the spacing between laterally adjacent holes is minimized whereby the opposing pairs of columns of threads 82 generally provide the structure between each laterally adjacent pair of holes 76.

Figure 12:
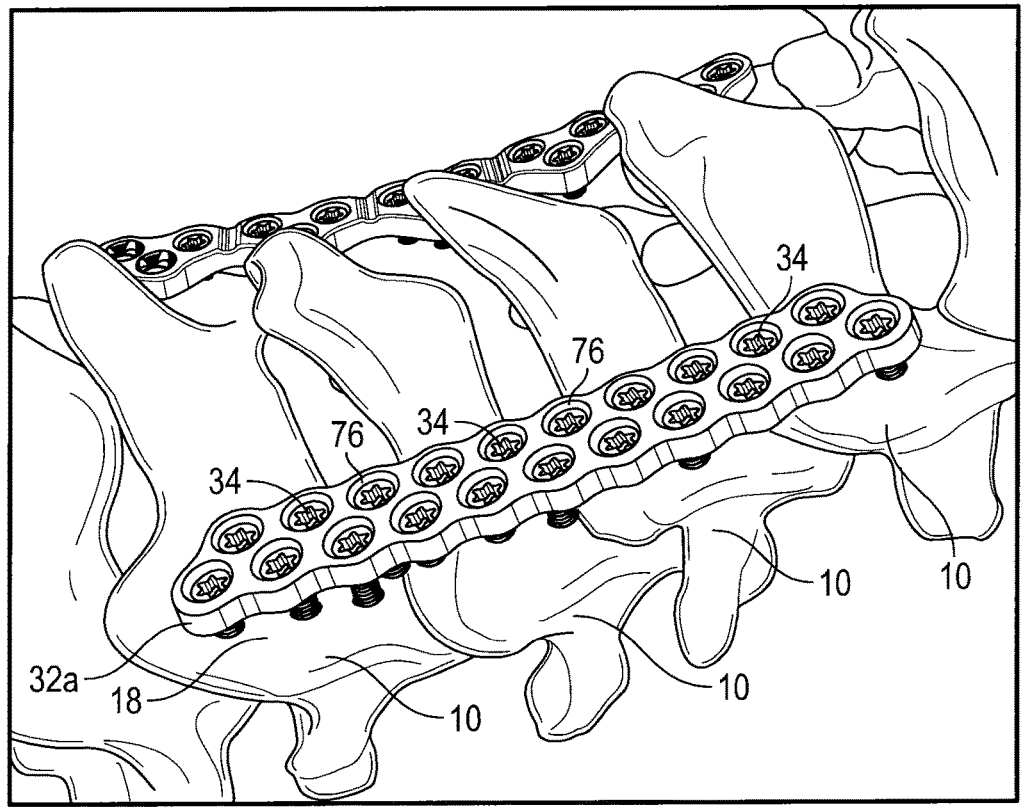
FIG. 12 is a posterior, perspective view of the bone plate of FIG. 8 shown connected to a plurality of vertebrae along one posterior side of the vertebrae.

FIG. 12 shows the bone plate 32a connected to the posterior side of a plurality of vertebrae 10 with the bone plates 32a extending along the posterior side of four vertebrae 10 adjacent the lateral masses 18 of each of the vertebrae 10 and the holes 76 being spaced in such a way that a plurality of holes 76 is positioned over the lateral mass 18 of each of the vertebrae 10 to define a plurality of fixation points to each of vertebrae 10. The attachment members 34 are inserted through selected holes 76 and into the lateral mass 18 of a corresponding vertebra 10 to fix the bone plate 32a to the vertebrae 10.

Figure 13A:
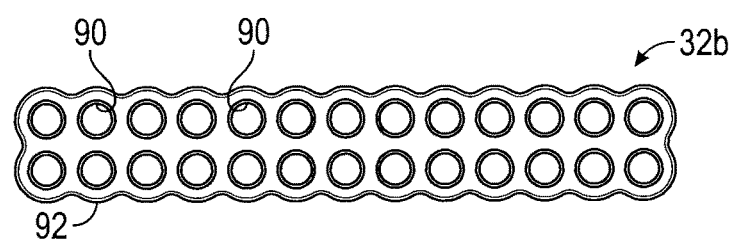
FIG. 13A is a top plan view of another embodiment of a bone plate constructed in accordance with the inventive concepts disclosed herein.

FIG. 13A shows another embodiment of a bone plate 32b constructed in accordance with the inventive concepts disclosed herein. The bone plate 32b is similar to the bone plate 32a, except that the bone plate 32b has a plurality of holes 90 arranged in two longitudinal rows with the holes 90 of each row positioned directly laterally of a hole 90 in the other row. The holes 90 are sized and spaced apart from one another such that two or more of the holes 90 are positionable or alignable over the lateral mass of a single vertebra to define a plurality of fixation points per vertebra. Further, the bone plate 32b is illustrated as having a perimeter edge 92 extending between the upper surface and the lower surface which is configured to substantially conform to the contour of the holes 90 of the of the bone plate 32b to define a plurality of nodules and recesses.

Figure 13B:
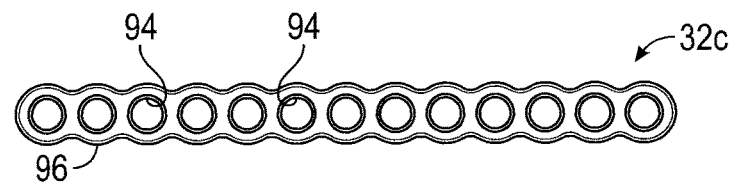
FIG. 13B is a top plan view of another embodiment of a bone plate constructed in accordance with the inventive concepts disclosed herein.

FIG. 13B shows a version of a bone plate 32c constructed in accordance with the inventive concepts disclosed herein. The bone plate 32c is similar to the bone plate 32b, except that the bone plate 32b has a single longitudinal row of holes 94. The holes 94 are sized and spaced apart from one another such that at least two of the holes 94 are positionable or alignable over the lateral mass or lamina of a single vertebra to define a plurality of fixation points per vertebra. Further, the bone plate 32c has a perimeter edge 96 extending between the upper surface and the lower surface which is configured to substantially conform to the contour of the holes 94 of the of the bone plate 32c to define a plurality of nodules and recesses.

Figure 14:
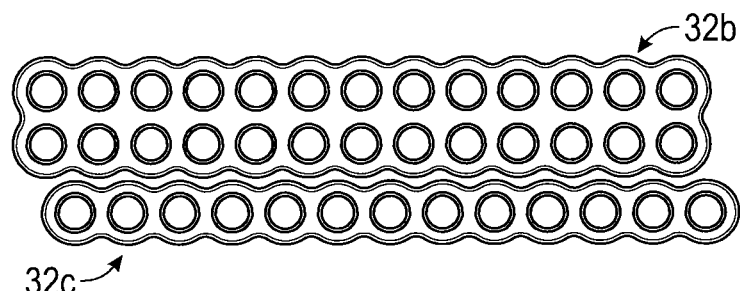
FIG. 14 is a top plan view illustrated the bone plate of FIG. 12 nested with the bone of FIG. 13.

FIG. 14 illustrates the bone plate 32b nested or engaged with the bone plate 32c along one side of corresponding edges of the bone plates 32b and 32c. In such an embodiment of paired bone plates 32b and 32c, the bone plate 32b can be attached to the lateral masses, while the bone plate 32c can be attached to the corresponding lamina.

Figure 15:
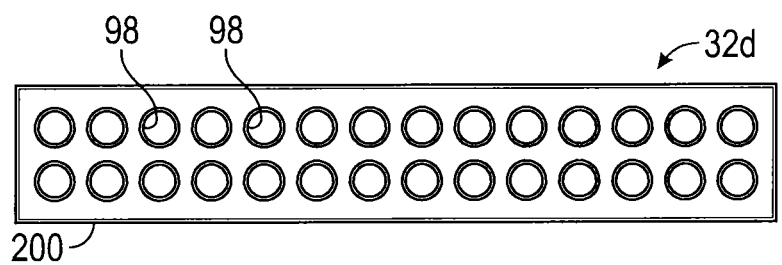
FIG. 15 is a top plan view of another embodiment of a bone plate constructed in accordance with the inventive concepts disclosed herein.

FIG. 15 illustrates another embodiment of a bone plate 32d constructed in accordance with the inventive concepts disclosed herein. The bone plate 32d is similar to the bone plate 32b. That is, the bone plate 32d has a plurality of holes 98 arranged in two longitudinal rows with the holes 98 of each row positioned directly laterally of a hole 98 in the other row. The holes 98 are sized and spaced apart from one another such that at least two of the holes 98 are positionable or alignable over the lateral mass or lamina of a single vertebra to define a plurality of fixation points per vertebra. However, the bone plate 32d is illustrated as having a perimeter edge 200 extending between the upper surface and the lower surface which is substantially straight or non-contoured.

Figure 16:
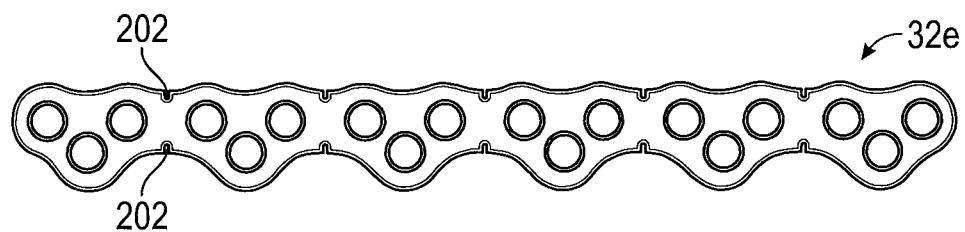
FIG. 16 is a top plan view of another embodiment of a bone plate constructed in accordance with the inventive concepts disclosed herein.

FIG. 16 illustrates another embodiment of a bone plate 32e constructed in accordance with the inventive concepts disclosed herein. The bone plate 32e is similar to the bone plate 32 illustrated in FIG. 3, except that the bone plate 32e is shown to have vertically-oriented grooves 202 extending along either or both outer edges from the upper surface to the lower surface to facilitate bending of the bone plate 32e along a coronal plane.

Figure 17:
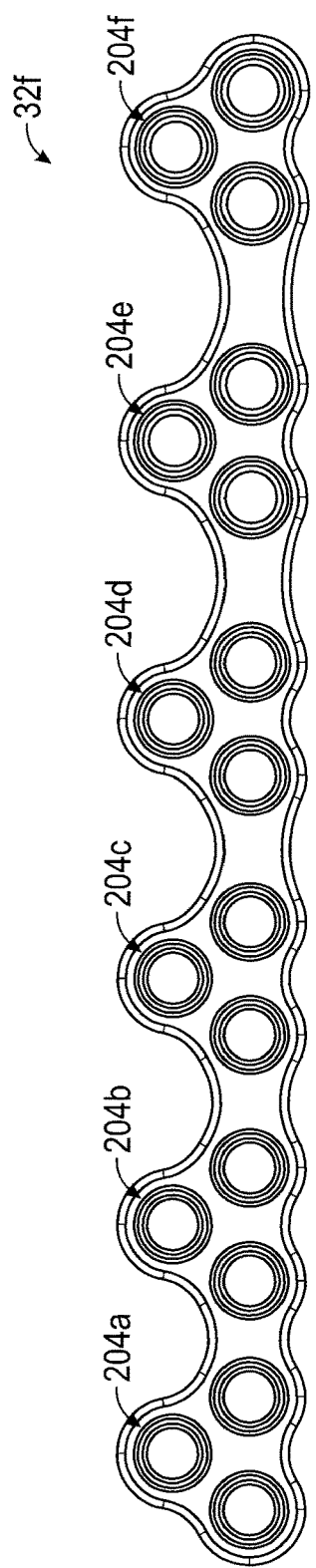
FIG. 17 is a top plan view of another embodiment of a bone plate constructed in accordance with the inventive concepts disclosed herein.

FIG. 17 illustrates another embodiment of a bone plate 32f constructed in accordance with the inventive concepts disclosed herein. The bone plate 32f is similar to the bone plate 32 illustrated in FIG. 3, except that the bone plate 32f has a plurality of groups of holes 204a-204f and the distance which the groups of holes 204a-204f are spaced from one another increases sequentially from one end of the bone plate 32f to the other end. By way of example, as measured from node to node, the groups of holes 204a-204f may be spaced at intervals of 13 mm, 14 mm, 15 mm, 16 mm, and 17 mm.

Figure 18:
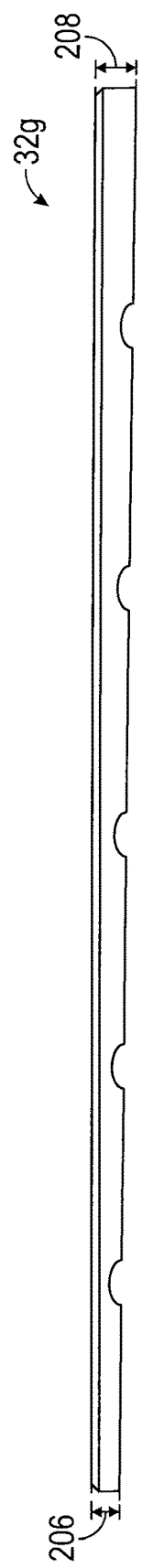
FIG. 18 is a side elevational view of another embodiment of a bone plate constructed in accordance with the inventive concepts disclosed herein.

FIG. 18 illustrates another embodiment of a bone plate 32g constructed in accordance with the inventive concepts disclosed herein. The bone plate 32g is similar to the bone plate 32 illustrated in FIG. 3, except that the bone plate 32g is tapered along a longitudinal axis such that one end of the bone plate 32g has a minor thickness 206 which is less thick than the other end which has a major thickness 208. By way of example, the minor thickness 206 may be 1.85 mm and the major thickness 208 may be 2.65 mm.

Figure 19:
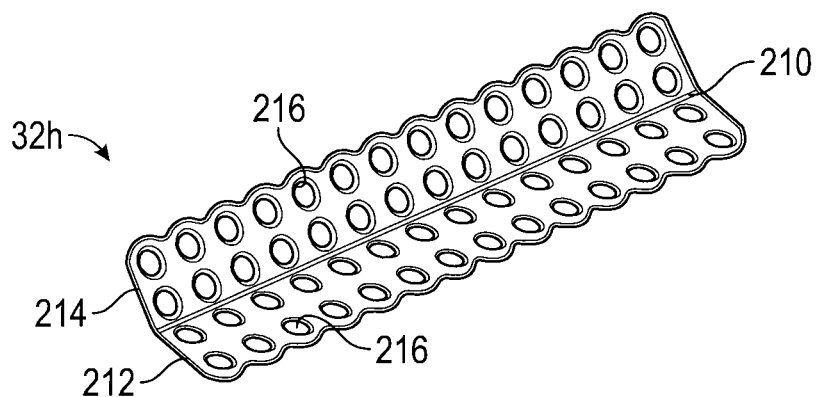
FIG. 19 is a top perspective view of another embodiment of a bone plate constructed in accordance with the inventive concepts disclosed herein.
Figure 20:
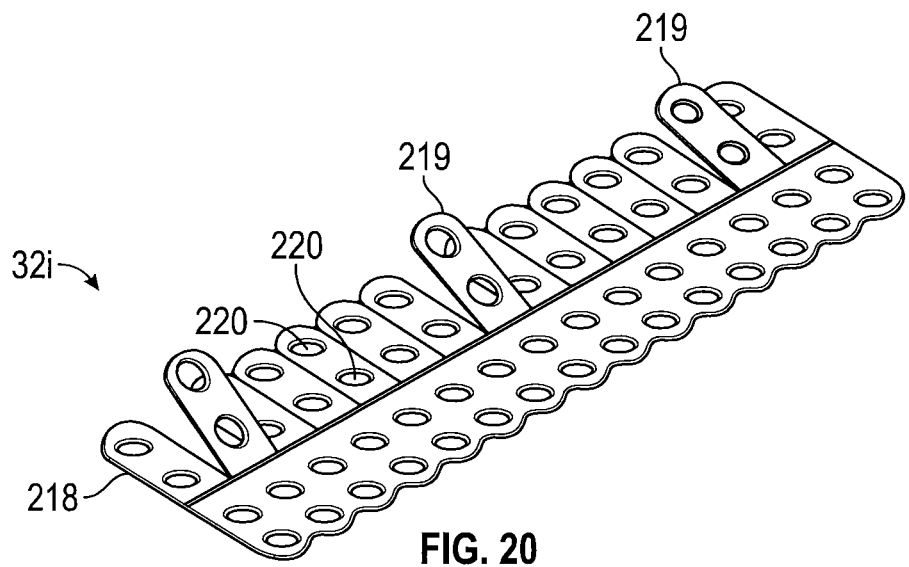
FIG. 20 is a top perspective view of another embodiment of a bone plate constructed in accordance with the inventive concepts disclosed herein.
Figure 21:
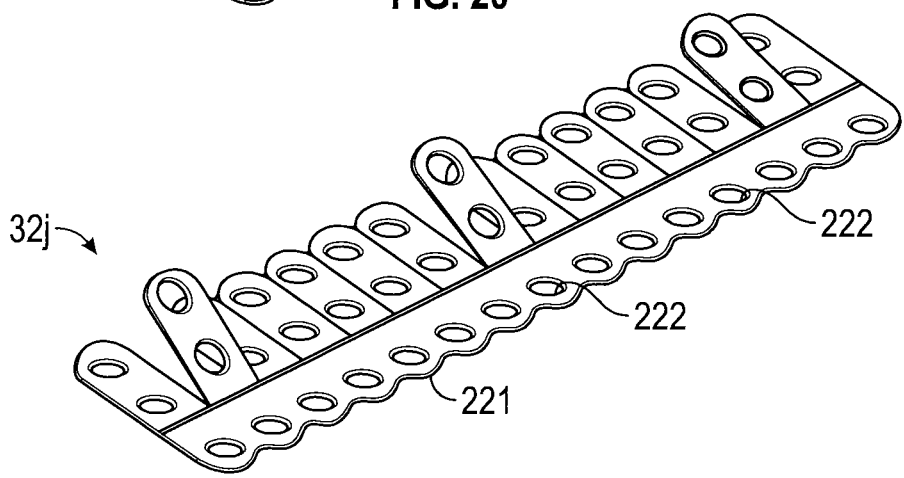
FIG. 21 is a top perspective view of another embodiment of a bone plate constructed in accordance with the inventive concepts disclosed herein.

FIGS. 19-21 illustrate bone plates 32h, 32i, and 32j constructed in accordance with the inventive concepts disclosed herein. The bone plate 32h, 32i, and 32j are configured to be bent along a longitudinal axis. The bone plate 32h has longitudinal groove 210 to facilitate bending of the bone 32h so as to define a lateral mass plate portion 212 and a lamina plate portion 214. The lateral mass plate portion 212 and the lamina plate portion 214 each have a plurality of holes 216 arranged in two longitudinal rows such the lateral mass plate portion 212 is attachable to the lateral masses of the corresponding vertebrae and the lamina plate portion 214 is attachable to the lamina of the corresponding vertebra with suitable attachment members.

The bone plate 32i is similar to the bone plate 32h except the bone plate 32i has a lamina plate portion 218 which has a plurality of tabs 219 which are individually bendable relative to the other tabs 219. Each tab 219 is shown as having two holes 220 for receiving attachment members.

The bone plate 32j is similar to the bone plate 32i, except the bone plate 32j has a lateral mass plate portion 221 shown to have a plurality of holes 222 arranged in a single longitudinal row for receiving attachment members.

Figure 22A:
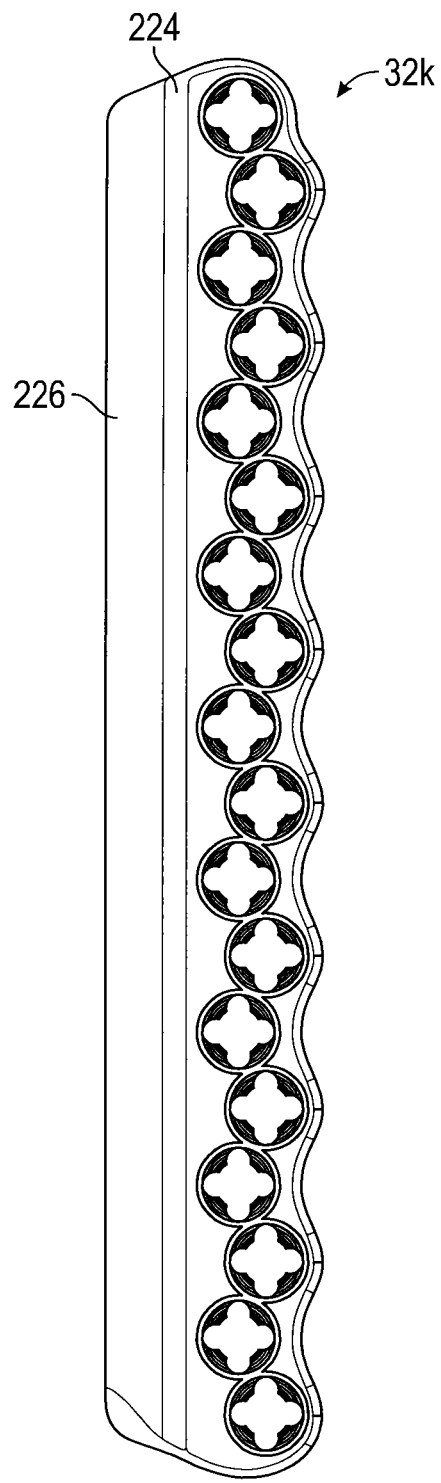
FIG. 22A is a top plan view of another embodiment of a bone plate constructed in accordance with the inventive concepts disclosed herein having a rod portion incorporated therein.
Figure 22B:
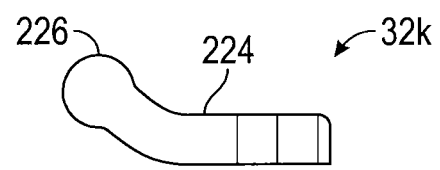
FIG. 22B is an end elevational view of the bone plate of FIG. 22A.
Figure 23A:
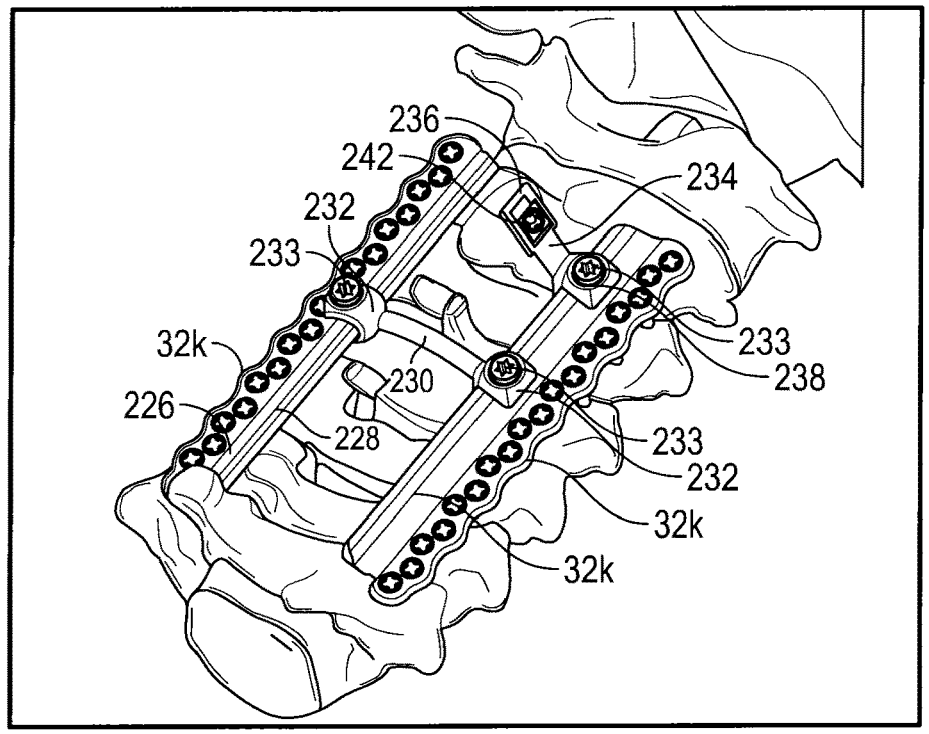
FIG. 23A is a perspective view of a pair of the bone plates of FIG. 22A shown connected to the posterior side of a plurality of vertebra and interconnected with a cross-linking connector and showing a lamina connector connected to one of the bone plates.

Referring now to FIGS. 22A, 22B, and 23A, another embodiment of a bone plate 32k constructed in accordance with the inventive concepts disclosed herein is illustrated. The bone plate 32k is shown as being similar to the bone plate 32a described above except that the bone plate 32k has a longitudinal edge 224 and a rod portion 226 formed along the inner longitudinal edge 224. Besides providing added strength and stiffness to the bone plate 32k, the rod portion 226 may serve as an attachment point for auxiliary implements. For example, as illustrated in FIG. 23A, the rod portion 226 may be used as a point of attachment for a cross-linking connector 228. The cross linking connector 228 may include a rod portion 230 and a rod engaging portion 232 formed on each end of the rod portion 230. The rod engaging portions 232 may be in the form of a C-shaped clamp mateable with the rod portion 230 of the bone plate 32k and a securement member, such as a set screw 233. The rod portion 230 has a length (or may configured for selective translation) so that the rod portion 230 extends from one side of a vertebra to an opposing side of the vertebra when one of the rod engaging portions 232 is engaged with the rod portion 226 of the bone plate 32k and the bone plate 32k is connected to the lateral masses of a plurality of vertebrae and the other rod engaging portions 232 is engaged with the rod portion 226 of another bone plate 32k and the other bone plate 32k is connected to the opposing lateral masses of the vertebrae.

The rod portion 226 may also be used as a point of attachment for a lamina connector 234 for fixing an arch during a laminoplasty procedure. As shown in FIG. 23A, the lamina connector 234 may have a plate portion 236 and a rod engaging portion 238. The rod engaging portion 238 may be in the form of a C-shaped clamp mateable with the rod portion 230 of the bone plate 32k and a securement member, such as a set screw 233. The plate portion 236 has a hole for receiving an attachment member, such as a screw 242. The plate portion 236 may be configured to for translation in a manner well known in the art. The plate portion 236 is positionable over a lamina of a vertebra and when the rod engaging portion 238 is engaged with the rod portion 236 of the bone plate 32k and the bone plate 32k is connected to the lateral masses of a plurality of vertebrae.

Figure 23B:
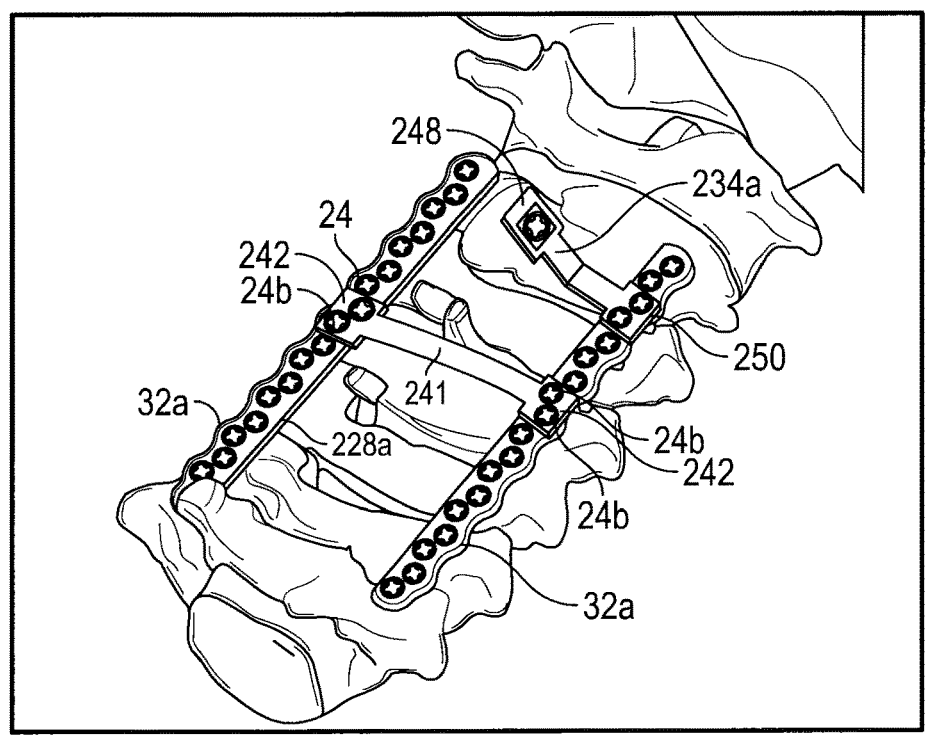
FIG. 23B is a perspective view of another embodiment pair of bone plates shown connected to the posterior side of a plurality of vertebra and interconnected with another embodiment of a cross-linking connector and showing another embodiment of a lamina connector connected to one of the bone plates.

FIG. 23B illustrates alternative embodiments of a cross linking connector 228a and a lamina connector 234a which are similar to the cross linking connector 228 and the lamina connector 234, respectively, except that the cross linking connector 228a and the lamina connector 234a are configured to be attached to a bone plate, such as the bone plate 32a, employing the holes 76 of the bone plate 32a used for fixing the bone plate 32a to vertebra or to alternative holes (not shown) which may be provided in the bone plate for attaching auxiliary implements thereto.

The cross linking connector 228a includes a rod portion 241 and a plate portion 242 formed on each end of the rod portion 241. The plate portions 242 are shown as being provided with a plurality of holes which are alignable with a plurality of holes 76 of the bone plates 32a such that the plate portions 244 may be attached to the upper surface of the bone plates 32a with a plurality of attachment members, such as screws 246.

Similarly, the lamina connector 234a may include a first plate portion 248 and a second plate portion 250 where the second plate portion 250 is similar in construction and function to the plate portion 242 described in reference to the cross linking connector 228a.

Figure 23C:
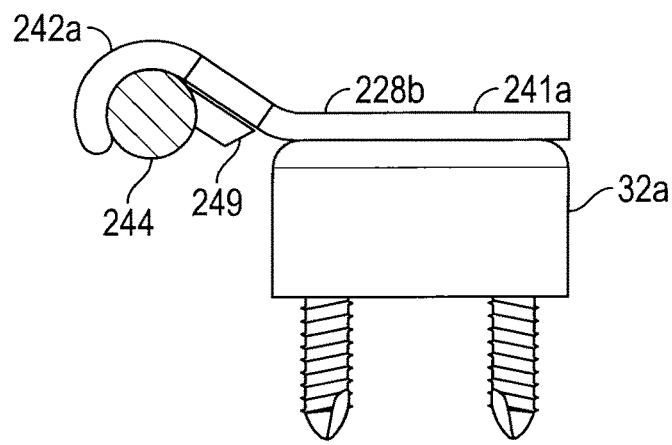
FIG. 23C is an end elevational view of a portion of the bone plate of FIG. 8 shown with a linking connector connected thereto.
Figure 23D:
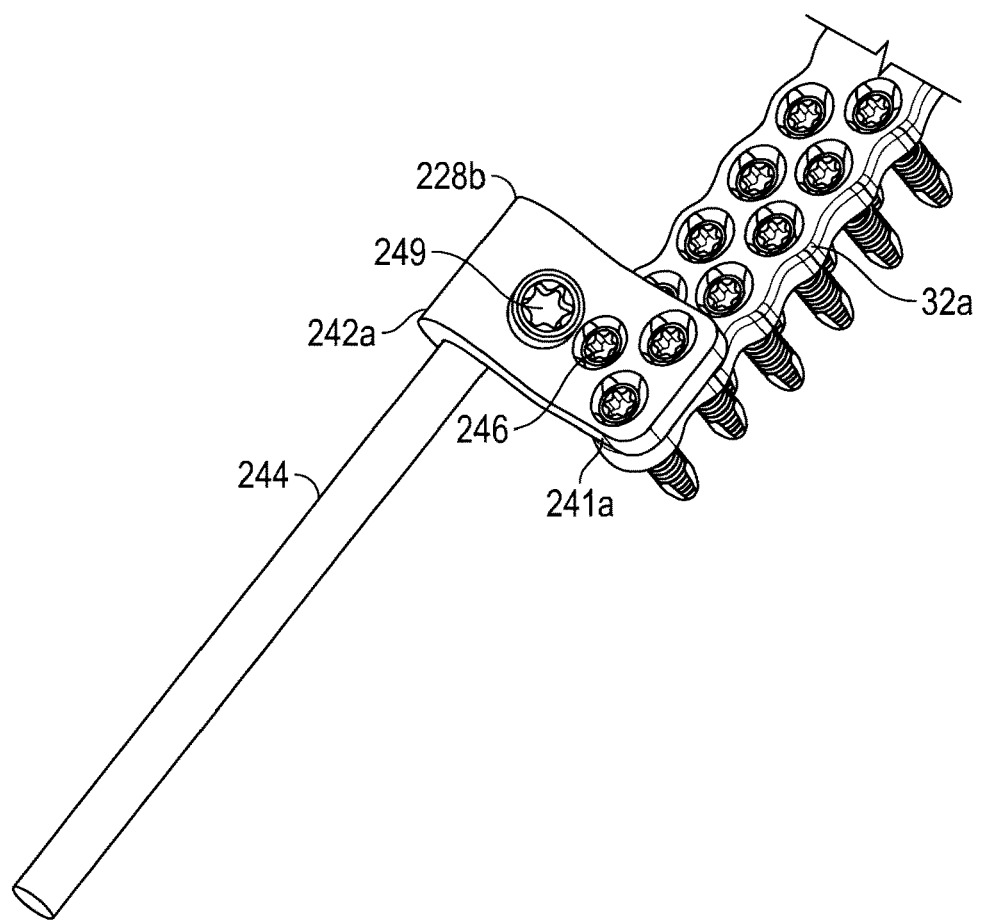
FIG. 23D is a perspective view of the linking connector of FIG. 23C shown connected to the bone plate of FIG. 8.

FIGS. 23C and 23D illustrate an embodiment of a linking connector 228b which is similar to the cross linking connector 228a, except that the linking connector 228b includes plate portion 241a and a rod receiving member 242a. The plate portion 241a is provided with a plurality of holes which are alignable with a pair of holes 76 of the bone plate 32a such that the plate portion 241a may be attached to the upper surface of the bone plate 32a with a plurality of attachment members, such as screws 246.

When the plate portion 241a is connected to the bone plate 32a, the rod receiving member 242a is oriented to receive a rod 244 which is longitudinally extended along the spine to be positioned so as to be connectable to other implements implanted in other vertebrae to which the bone plate 32a is not directly attached, such as one or more polyaxial screws. The rod 244 may be secured in the rod receiving member 241a with an attachment member, such as a set screw 249.

Figure 24:
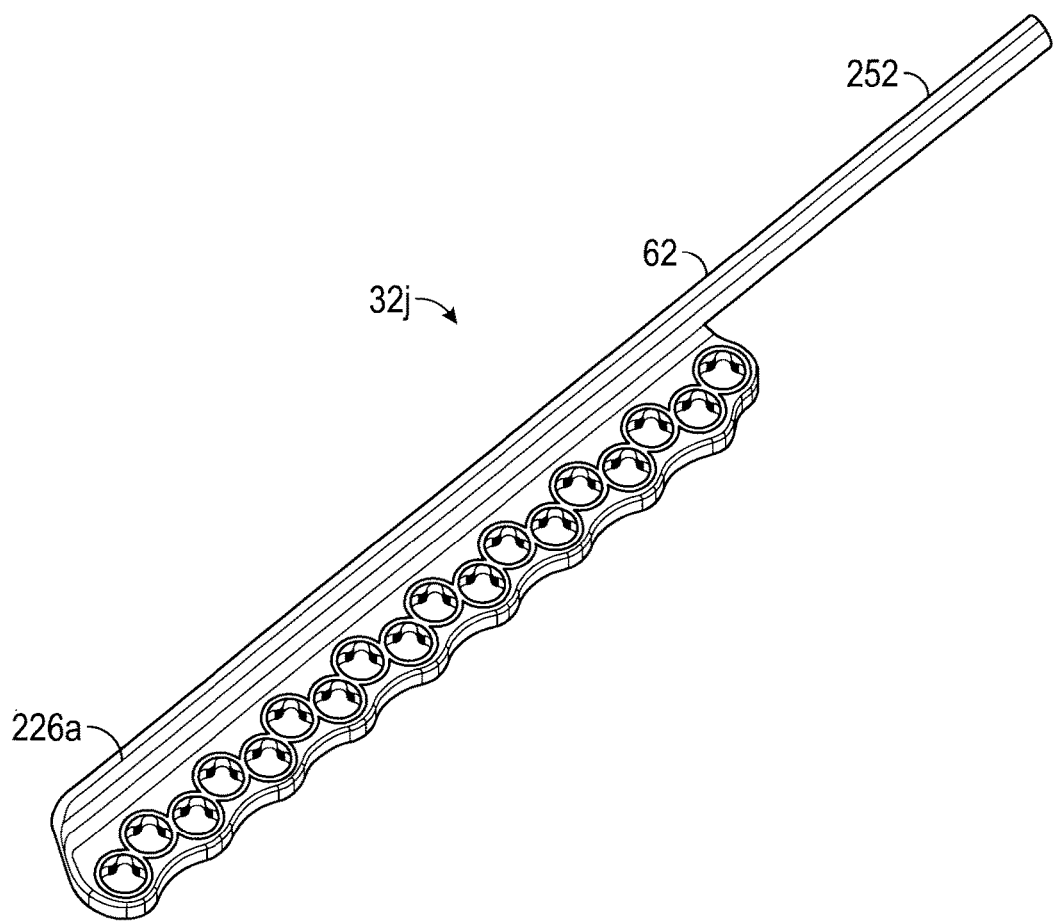
FIG. 24 is a perspective view of another embodiment of a bone plate constructed in accordance with the inventive concepts disclosed herein having a rod portion incorporated therein.

FIG. 24 illustrates another embodiment of a bone plate 32j constructed in accordance with the inventive concepts disclosed herein. The bone plate 32j is similar to the bone plate 32k described above, except the bone plate 32j has a rod portion 226a formed along a longitudinal edge of the bone plate 32j such that the rod portion 226a may serve as an attachment point for auxiliary implements. The rod portion 226a further has a rod extension portion 252 which extends a distance beyond at least one end of the bone plate 32k so as to be connectable to other implements implanted in other vertebrae to which the bone plate 32j is not directly attached, such as one or more polyaxial screws. To this end, the rod extension portion 252 may be configured to be positioned in a rod receiving head of polyaxial screw assembly in a manner similar to the way a spinal rod (not shown) would be positioned in a rod receiving head of a polyaxial screw assembly. It should be appreciated that the length of the rod extension portion 252 may be varied during manufacture or customized prior to attachment to a patient.

Figure 25A:
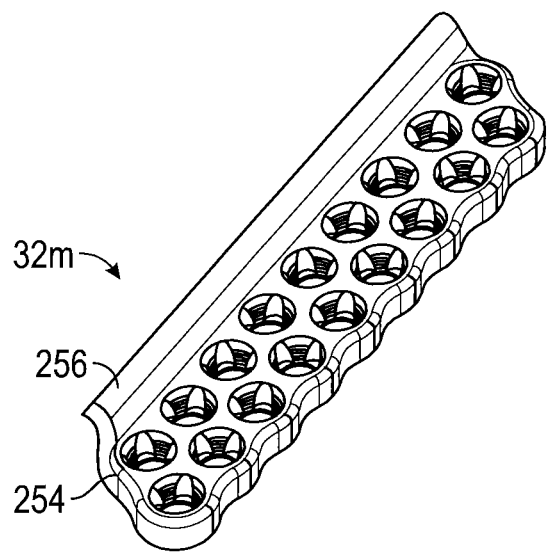
FIG. 25A is a perspective of another embodiment of a bone plate constructed in accordance with the inventive concepts disclosed herein.
Figure 25B:
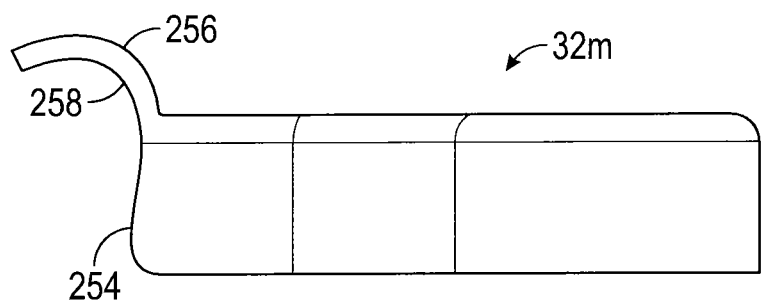
FIG. 25B is an end elevational view of the bone plate of FIG. 25A.

Referring now to FIGS. 25A and 25B, another embodiment of a bone plate 32m constructed in accordance with the inventive concepts disclosed herein is illustrated. The bone plate 32m is illustrated as being similar in construction to the bone plate 32a described above, except the bone plate 32m has an outer longitudinal edge 254 with a bone graft ridge 256 extending upwardly and outwardly from the outer longitudinal edge 254 of the bone plate 32m. The bone graft ridge 256 functions to define a pocket or void 258 in cooperation with the surface of the vertebrae so that biologic material may be packed in the pocket 258 to facilitate the formation of a graft between two vertebrae. Such biologic material can include, but is not limited to, medicine, human tissue, animal tissue, synthetic tissue, human cells, animal cells, synthetic cells, and the like.

Figure 25C:
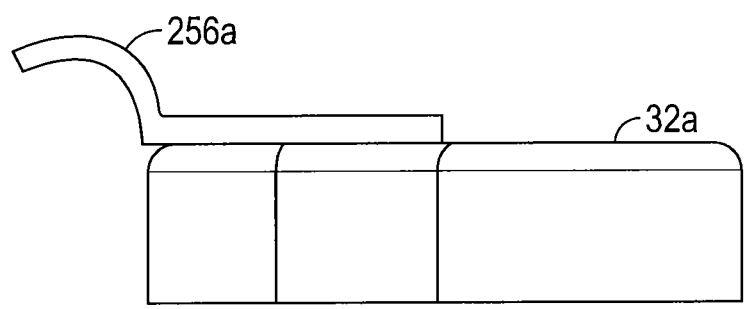
FIG. 25C is an end elevational view of the bone plate of FIG. 8 shown with a bone graft ridge connected thereto.

FIG. 25C illustrates another version of a bone graft ridge 256a which is formed by a separate piece which may be connected to a bone plate, such as the bone plate 32a, in any suitable fashion, such as with screws (now shown).

Figure 26:
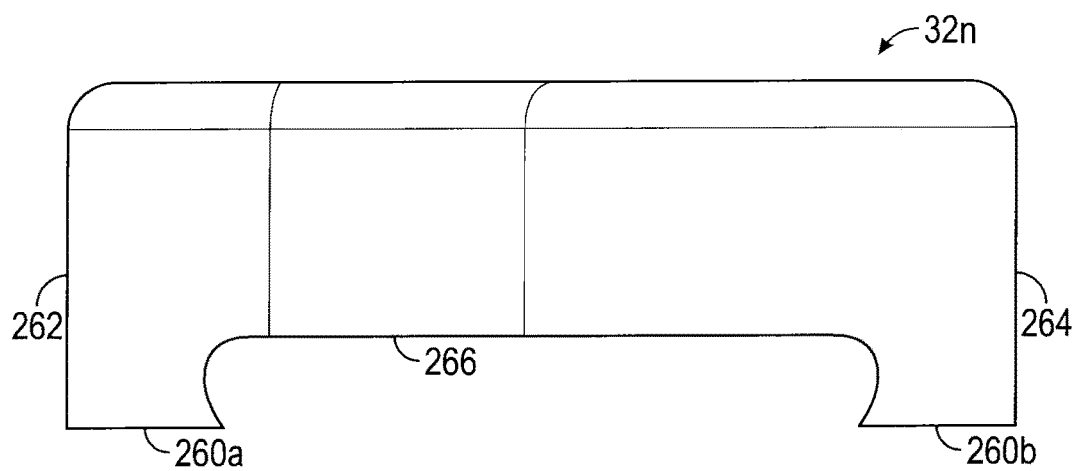
FIG. 26 is an end elevational view of another embodiment of a bone plate constructed in accordance with the inventive concepts disclosed herein.

FIG. 26 illustrates another embodiment of a bone plate 32n constructed in accordance with the inventive concepts disclosed herein. The bone plate 32n is similar to the bone plates described above, except the bone plate 32n has a pair of flanges 260a and 260b extending downwardly from the lower surface thereof along an inner longitudinal edge 262 and an outer longitudinal edge 264 so as to define a pocket 266 in which biologic material may be packed to facilitate the formation of a graft between two vertebrae.

Figure 27:
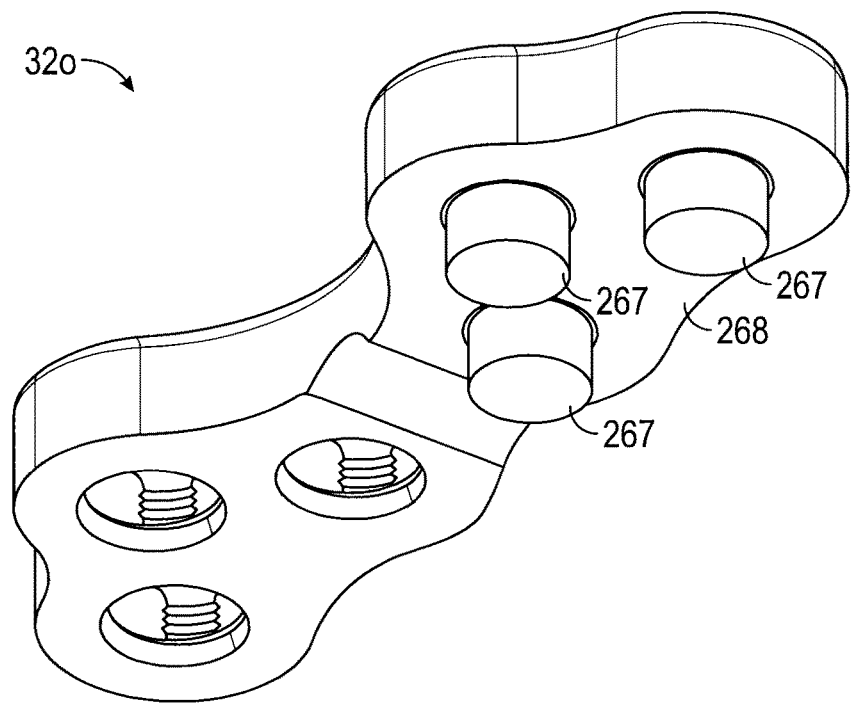
FIG. 27 is a lower perspective view of another embodiment of a bone plate constructed in accordance with the inventive concepts disclosed herein having bosses formed thereon for engagement with an adjacent bone plate.

FIG. 27 illustrates another embodiment of a bone plate 32o that is similar to the plates discussed above, except that the bone plate 32o is provided with a plurality of protrusions 267 extending from a lower side 268 of the bone plate 32o near one end thereof. The protrusions 267 are configured and arranged to align with and fit in a group of holes of another bone plate in such a way that the two plates may be interlocked with one another. The bone plate 32o may be contoured so that the bone plate 32o may be positioned on another bone plate in an overlapping relationship, while permitting the bone plate 32o to be attached to vertebrae in the manner discussed above with attachment members 34.

Figure 28:
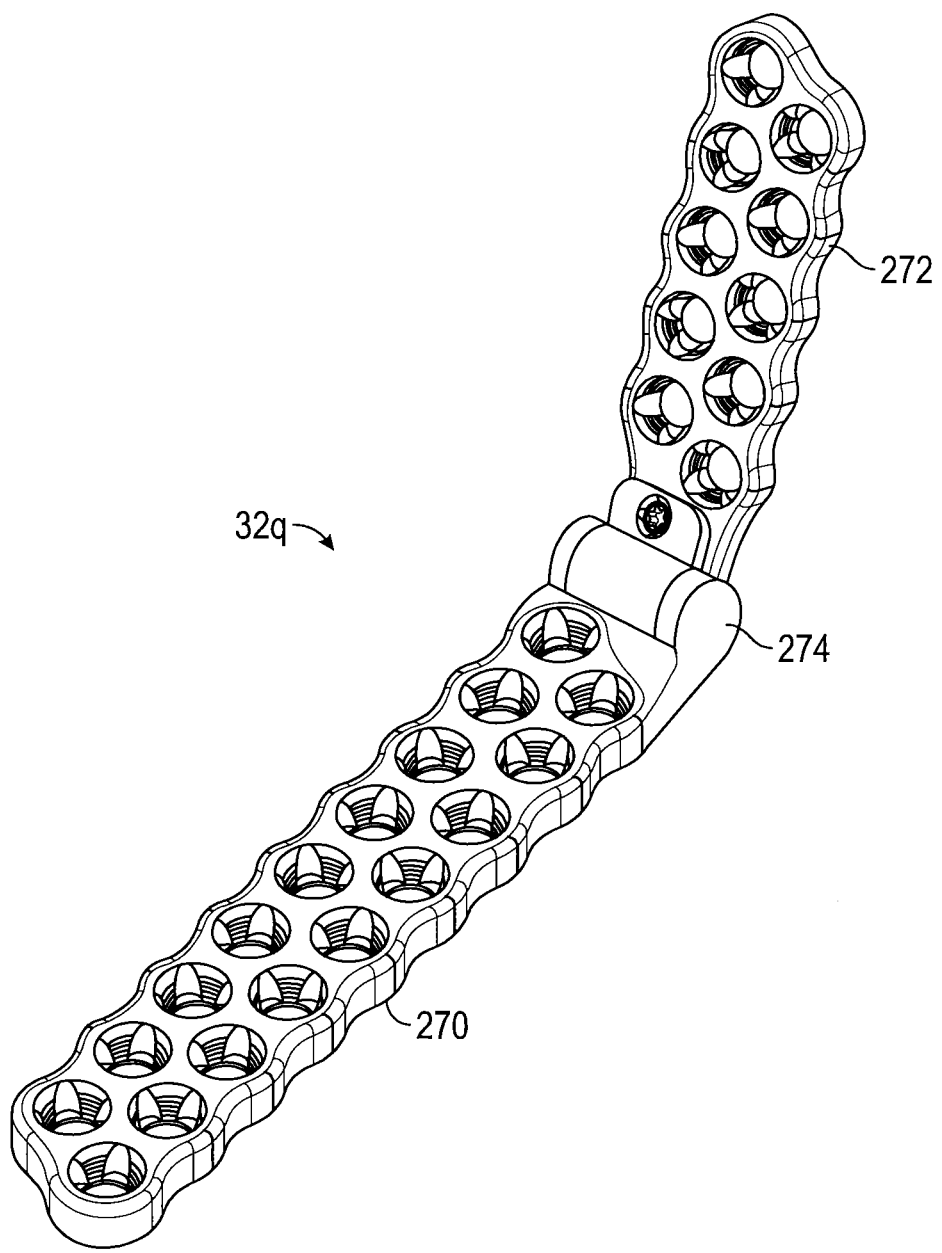
FIG. 28 is a perspective view of another embodiment of a bone plate constructed in accordance with the inventive concepts disclosed herein.

FIG. 28 illustrates yet another embodiment of a bone plate 32q constructed in accordance with the inventive concepts disclosed herein. The bone plate 32q includes a first plate portion 270 and a second plate portion 272. By way of example, the first plate portion 270 and the second plate portion 272 are illustrated as being similar in configuration to the bone plate 32a described above. The first plate portion 270 is longitudinally aligned with the second plate portion 272, and the first plate portion 270 is pivotally connected to the second plate portion 272. In one embodiment, the first plate portion 270 may be pivotally connected to the second plate portion 272 via a locking hinge 274 to allow the first plate portion 272 and the second plate portion 274 to be fixed in a desired angular relationship relative to one another, whether about a single axis or multiple axes, particularly when used for occipital-cervical fusion or deformity correction.

Figure 29A:
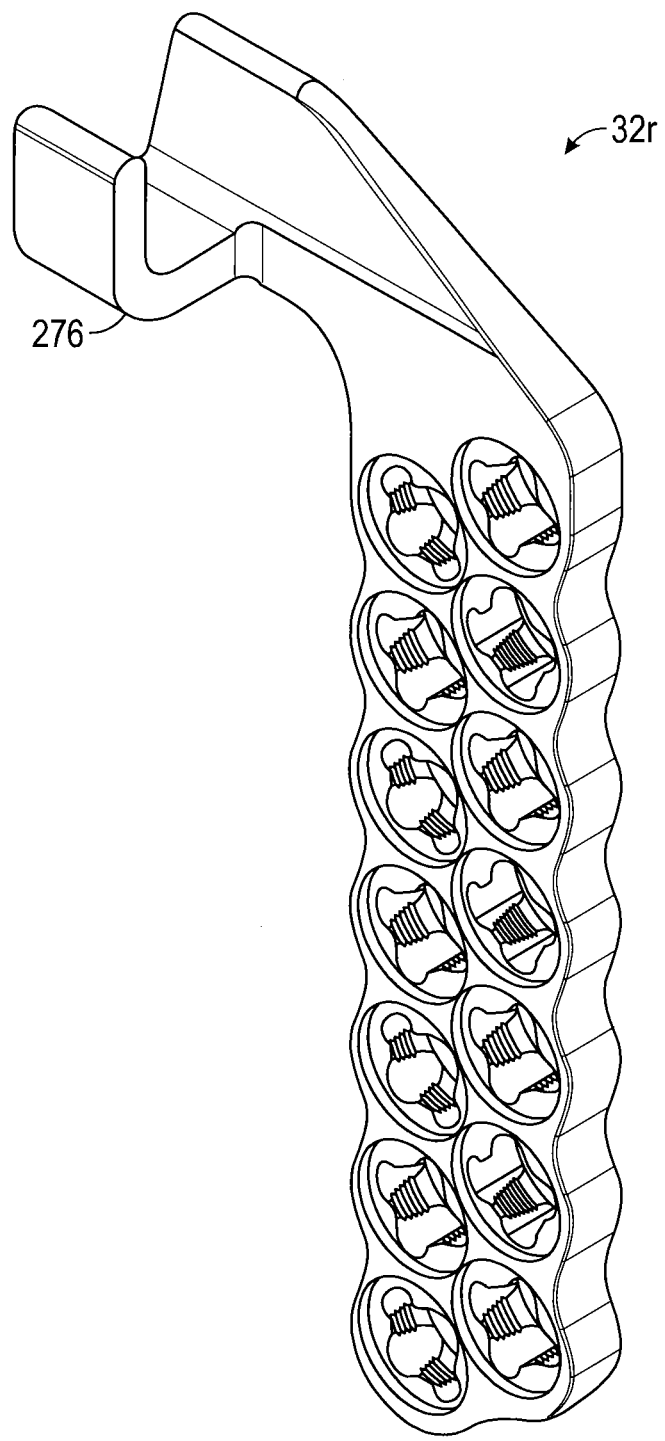
FIG. 29A is a perspective view of another embodiment of a bone plate constructed in accordance with the inventive concepts disclosed herein.
Figure 29B:
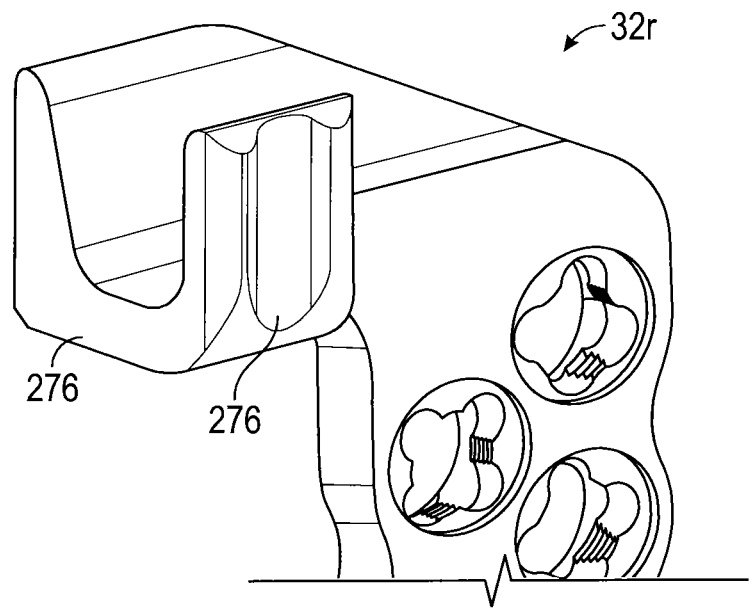
FIG. 29B is a perspective view of a portion of another version of the bone plate of FIG. 29A.

FIG. 29A is a bottom perspective view of another embodiment of a bone plate 32r constructed in accordance with the inventive concepts disclosed herein is illustrated. The bone plate 32r is illustrated as being similar in construction to the bone plate 32a, except the bone plate 32r is provided with a hook 276 extending substantially normal to the longitudinal axis of the bone plate 32r. The hook 276 is configured to be received on the posterior arch of the C1 vertebra when the bone plate 32r is connected to the adjacent vertebrae of the spine as discussed above. To this end, it should be appreciated that the hook 276 may be formed at various angles relative to the longitudinal axis of the bone plate 32r to be received at selected positions on the arch of the C1 vertebra. As shown in FIG. 29B, the bone plate 32r may be further provided with a retaining groove 278 formed on an outer surface of the hook 276 to retain a cable or wire (not shown) which may be extended about the hook 276 and the ring of the C1 vertebra to further hold the hook 276 in place on the ring.

Figure 30:
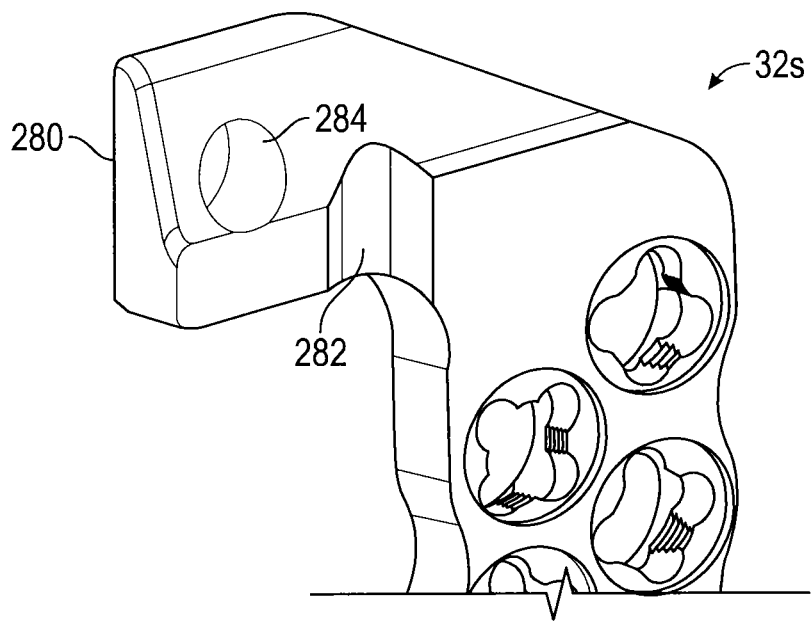
FIG. 30 is a perspective view of a portion of another embodiment of a bone plate constructed in accordance with the inventive concepts disclosed herein.

FIG. 30 illustrates another version of a bone plate 32s which is similar to the bone plate 32r except the bone plate 32s includes a platform 280 extending substantially normal to the longitudinal axis of the bone plate 32s. The platform 280 is configured to be positioned on the ring of the C1 vertebra when the bone plate 32s is connected to the adjacent vertebrae of the spine as discussed above. To this end, it should be appreciated that the hook platform 280 may be formed at various angles relative to the longitudinal axis of the bone plate 32s to be received at selected positions on the ring of the C1 vertebra. The platform 280 may be provided with a retaining groove 282 and a hole 284 retaining a cable (not shown) which may be extended about the through the hole 284, about the platform 280 along the retaining groove 282, and about the ring of the C1 vertebra to hold the platform 280 in place on the ring.

Figure 31A:
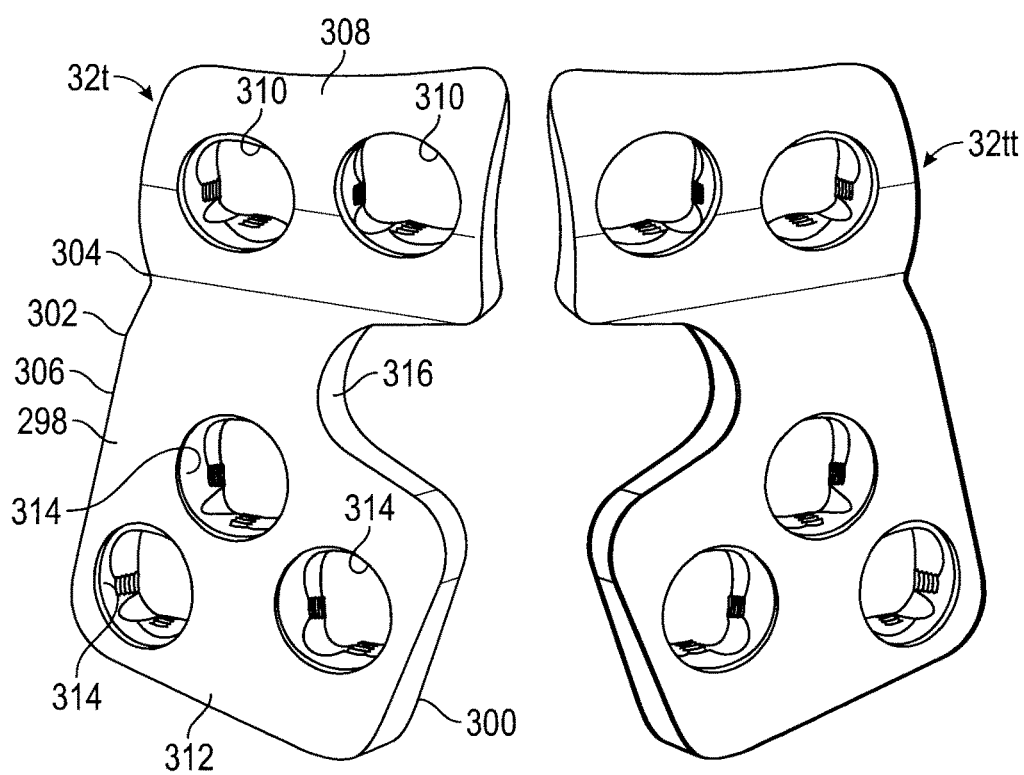
FIG. 31A is a perspective view of another embodiment of a pair of bone plates constructed in accordance with the inventive concepts disclosed herein.
Figure 31B:
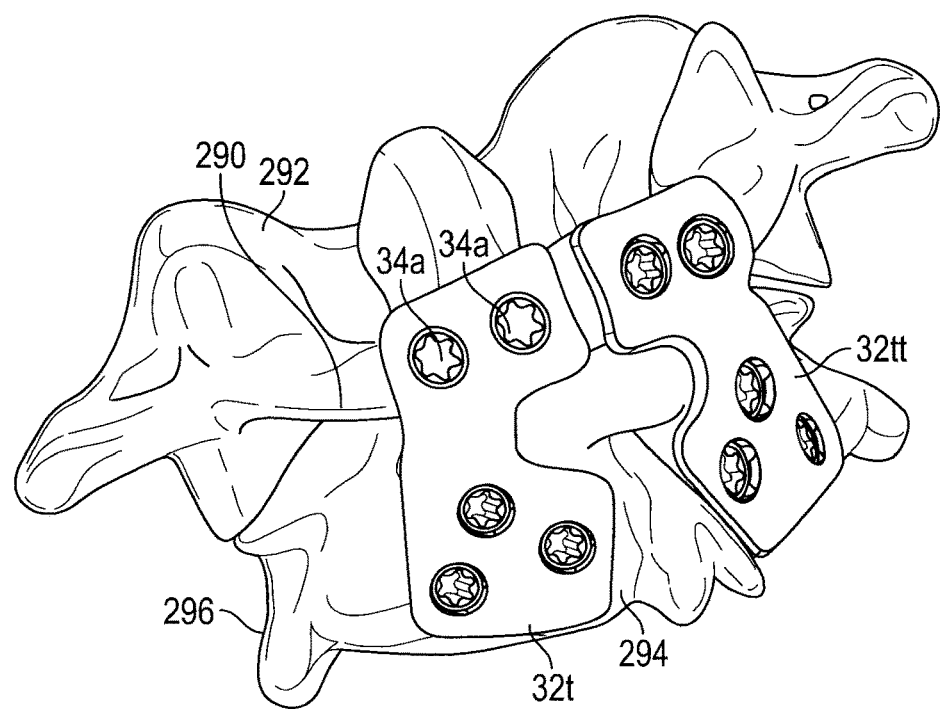
FIG. 31B is a perspective view illustrating the bone plates of FIG. 29A connected to the C1 and C2 vertebrae.

Referring now to FIGS. 31A and 31B, another embodiment of a pair of bone plate 32t and 32tt constructed in accordance with the inventive concepts disclosed herein is illustrated. The bone plates 32t and 32tt are identical in construction with the exception that the bone plate 32tt is a mirror image of the bone plate 32t. Therefore, only the bone plate 32t will be described in detail below. The bone plate 32t is intended to fuse or stabilize multiple vertebrae, more specifically the C1 and C2 vertebrae. The bone plate 32t is configured and dimensioned to extend along the posterior side of at least the C1 vertebra and the C2 vertebra, and particularly, the bone plate 32r is configured to extend from a posterior ring 290 of a C1 vertebra 292 to a lamina 294 of a C2 vertebra 296. It will be appreciated that the length of the bone plate 32t may be varied depending on the number of vertebrae to be stabilized beyond the C2 vertebra.

The bone plate 32t has an upper surface 298 and a lower surface 300. Like the bone plates described above, the lower surface 300 can be provided with a textured surface such that described above in reference to FIG. 4B which may include a variety of geometric shapes and/or protrusions, such as spikes, or other features, such as ridges, posts, pockets, or be treated such as bead blasted or acid etched to enhance its grip on the vertebral body.

The bone plate 32t has a spacer portion 302 having a first end 304 and a second end 306. The longitudinal length of the spacer portion 302 generally corresponds to the distance between the ring 290 of the C1 vertebra 292 and the lamina 294 of the C2 vertebra 296.

A ring engaging portion 308 extends from the first end 304 of the spacer portion 308. The ring engaging portion 308 is configured to extend along and conform to at least a portion of the ring 290 of the C1 vertebra 292. More specifically, the ring engaging portion 308 has an arcuate profile such that the ring engaging portion 308 substantially conforms to the contour of the ring 290 of the C1 vertebra 292. The ring engaging portion 308 has a width such that a plurality of holes 310 may be formed in the ring engaging portion 310 in such a way that at least two holes are positionable over the posterior side of the ring 290 of the C1 vertebra 292. The holes 310 may be threaded or non-threaded similar to the holes 56 and 76 discussed above to receive an attachment member, such as attachment members 34.

A lamina engaging portion 312 extends from the second end 306 of the spacer portion 302. The lamina engaging portion is configured to extend along and conform to a portion of the posterior side of the C2 vertebra 296, e.g., the lamina, the lateral mass, or a combination of the lamina and the lateral mass. As illustrated in FIGS. 31A and 32B, the lamina engaging portion 312 has a flatter profile than the ring engaging portion 308 so that the lamina engaging portion 312 substantially conforms to the contour of the lamina 294 of the C2 vertebra 296. The lamina engaging portion 312 has a width such that a plurality of holes 314 are formed in the lamina engaging portion 312 in such a way that at least two holes are positionable over the lamina 294 of the C2 vertebra 296. The holes 312 may be threaded or non-threaded similar to the holes 56 and 76 discussed above to receive an attachment member, such as attachment members 34.

In one exemplary embodiment, the spacer portion 302 has a width that is less than the width of the ring engaging portion 308 and the width of the lamina engaging portion 312 so as to define a notch or window 316 along an inside edge of the bone plate 32t. The window 316 allows direct visualization of the central canal, as well as facilitates identifying the difference between the bone plate 32r and 32rr.

The holes 310 and 314 extend through the bone plate 32r from the upper surface 298 through the lower surface 300. The holes 310 and 314 may be entirely perpendicular to the plane of the bone plate 32t, or may be offset in the general direction which screw angulation is desired. For example, the holes 310 and 314 may be laterally outwardly angled, e.g., at an angle of approximately 10 to 30 degrees of lateral outward angulation.

The holes 310 are dimensioned and arranged relative to one another so that more than one of the holes 310 are positionable or alignable over the ring 290 of the C1 vertebra 292 to define a plurality of fixation points to the C1 vertebra 292, and the holes 314 are dimensioned and arranged relative to one another so that more than one of the holes are positionable or alignable over the lamina 294 of the C2 vertebra 296 to define a plurality of fixation points to the C2 vertebra 296. The holes 310 and 314 may be arranged in a variety of ways to provide multiple points of fixation.

The bone plate 32t and the holes 310 and 314 are shown to be sized and spaced is so that at least two of the holes 310 and 314 are positionable over each vertebra to which the bone plate 32t is to be coupled (considering one side of the spine only and depending on the particular vertebra to which the plate is coupled). Those of ordinary skill in the art will understand that sizing and spacing of the holes 302 may be varied to achieve a desired number of fixation points. By way of example, the holes 310 and 314 may have a diameter to accommodate a screw having an outer diameter in a range from about 1.5 mm to about 3.0 mm.

Like the holes 56 and 76 described above, the holes 310 and 314 are shown to be threaded to receive one of the attachment members 34a. Again, those skilled in the art will appreciate that any thread configuration may be used, including variable angle locking threads, or the holes 310 and 314 may even be non-threaded or smooth. Also, the holes 312 and 314 may be may be provided with flanges, as described above, to limit the extent of insertion of the attachment members 34.

Figure 32A:
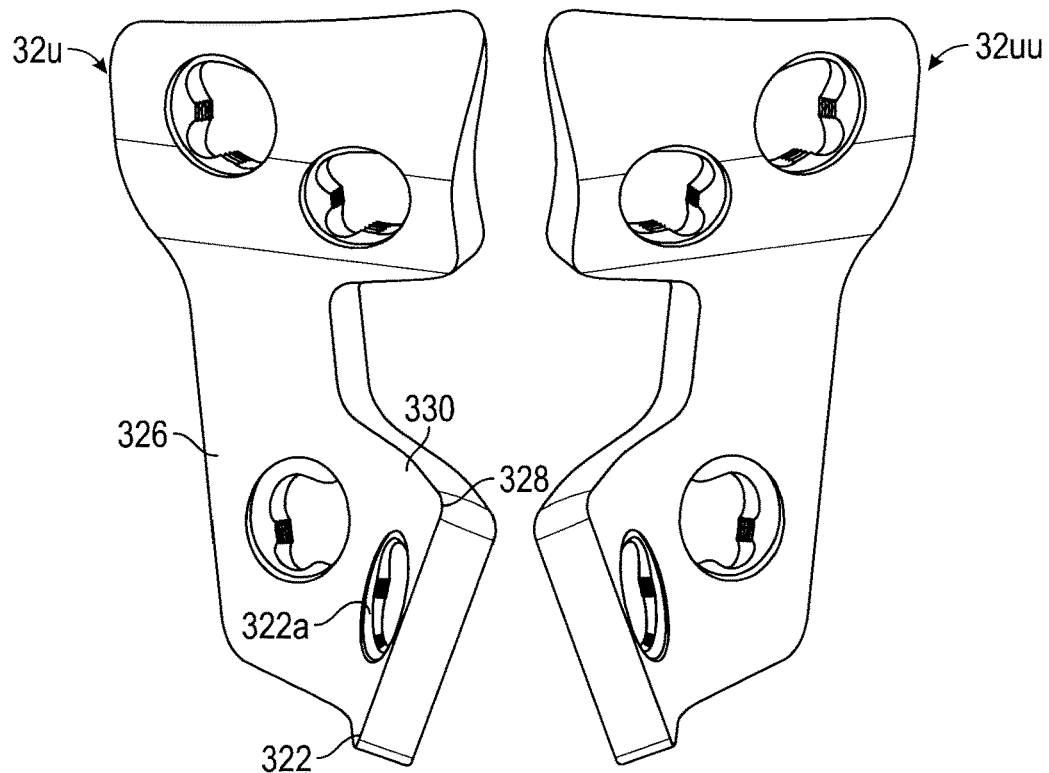
FIG. 32A is a perspective view of another embodiment of a pair of bone plates constructed in accordance with the inventive concepts disclosed herein.
Figure 32B:
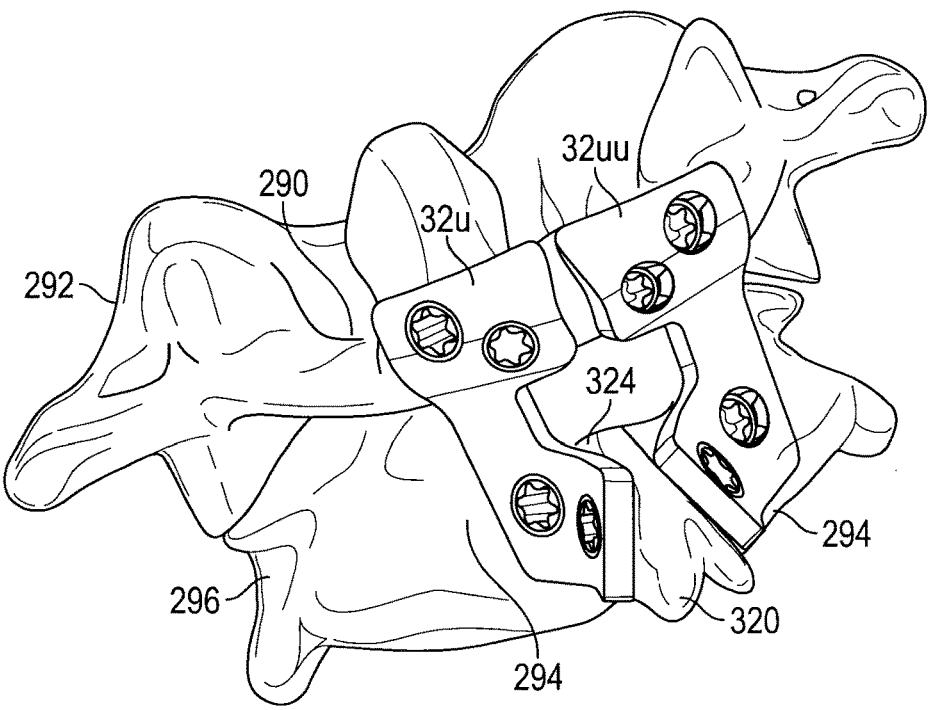
FIG. 32B is a perspective view illustrating the bone plates of FIG. 30A connected to the C1 and C2 vertebrae.

Referring now to FIGS. 32A and 32B, another embodiment of a pair of bone plate 32u and 32uu constructed in accordance with the inventive concepts disclosed herein is illustrated. The bone plate 32u and 32uu are identical in construction with the exception that the bone plate 32uu is a mirror image of the bone plate 32u. Therefore, only the bone plate 32u will be described in detail below. The bone plate 32u is intended to fuse or stabilize multiple vertebrae, more specifically the C1 and C2 vertebrae. To this end, the bone plate 32u is configured and dimensioned to extend along the posterior side of at least the C1 vertebra and the C2 vertebra. More specifically, the bone plate 32u is configured to extend from the posterior ring 290 of the C1 vertebra 292 to a juncture of the lamina 294 and spinous process 320 of the C2 vertebra 296. It will be appreciated that the length of the bone plate 32u may be varied depending on the number of vertebrae to be stabilized.

The bone plate 32u is similar to the bone plate 32t in construction and function, except that the bone plate 32u includes a translamina engaging portion 322 rather than a lamina engaging portion 312. The translamina engaging portion 322 is configured to extend along and conform to at least a portion of the lamina 296, a junction 324 of the lamina 296 and the spinous process 320, and the spinous process 320. The translamina engaging portion 322 has a lamina portion 326 and a spinous process portion 328 which are angled relative to one another to define a junction portion 330. The translamina engaging portion 322 has a width such that a plurality of holes 332 are formed in the translamina engaging portion 322 so that at least two holes are positionable over the combined area of the lamina 296 and the spinous process 320. In one embodiment, the translamina engaging portion 322 has at least one hole 332a located through the bone plate 32u at the junction portion 330 and oriented in such a way as to permit translaminar screw placement when the translamina engaging portion 322 is positioned on the lamina 296 and spinous process 320.

Figure 33A:
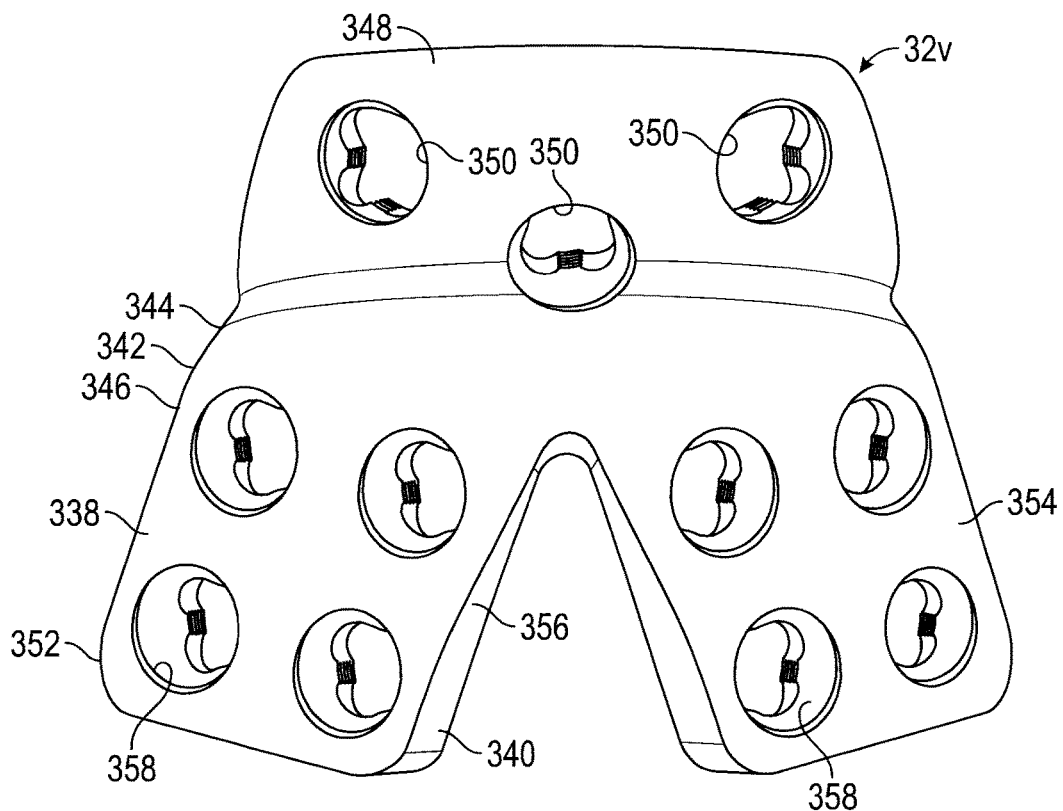
FIG. 33A is a perspective view of another embodiment of a pair of bone plates constructed in accordance with the inventive concepts disclosed herein.
Figure 33B:
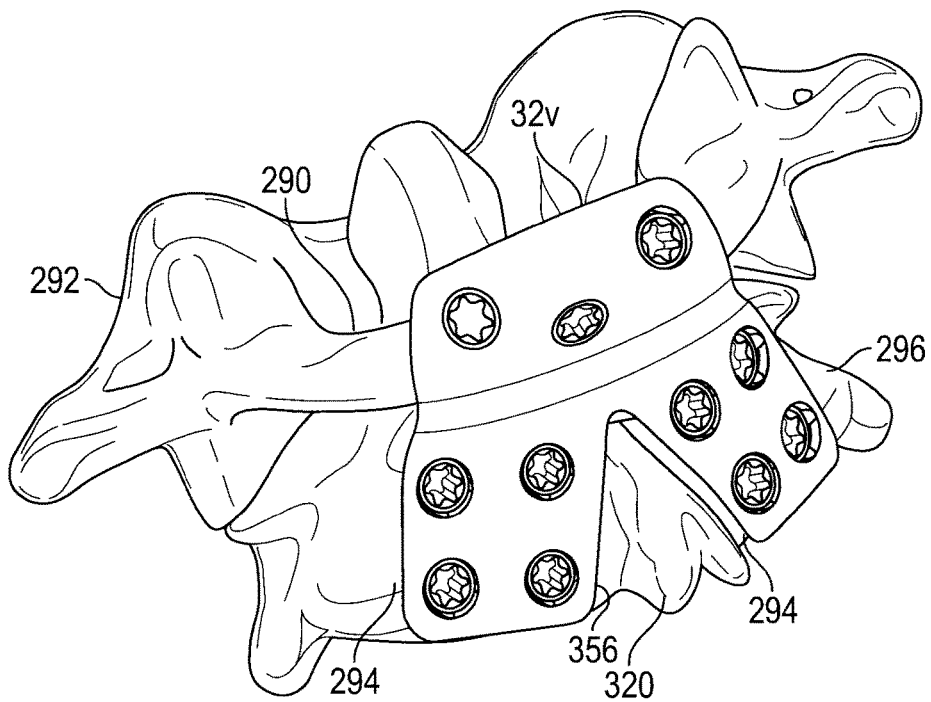
FIG. 33B is a perspective view illustrating the bone plates of FIG. 31A connected to the C1 and C2 vertebrae.

Referring now to FIGS. 33A and 33B, another embodiment of a bone plate 32v constructed in accordance with the inventive concepts disclosed herein is illustrated. The bone plate 32v is intended to fuse or stabilize multiple vertebrae, more specifically the C1 and C2 vertebrae. To this end, the bone plate 32v is configured and dimensioned to extend along the posterior side of at least the C1 vertebra 292 and the C2 vertebra 296. More specifically, the bone plate 32v is configured to extend from the posterior ring 290 of the C1 vertebra 292 to each lamina 294 of the C2 vertebra 292. It will be appreciated that the length of the bone plate 32v may be varied depending on the number of vertebrae to be stabilized.

The bone plate 32v has an upper surface 338 and a lower surface 340. Like the bone plates described above, the lower surface 338 can be provided with a textured surface such that described above in reference to FIG. 4B which may include a variety of geometric shapes and/or protrusions, such as spikes, or other features, such as ridges, posts, pockets, or be treated such as bead blasted or acid etched to enhance its grip on the vertebral body.

The bone plate 32v has a spacer portion 342 having a first end 344 and a second end 346. The longitudinal length of the spacer portion 342 generally corresponds to the distance between the ring 290 of the C1 vertebra 292 and the laminae 294 of the C2 vertebra 296.

A ring engaging portion 348 extends from the first end 344 of the spacer portion 348. The ring engaging portion 348 is configured to extend along and conform to at least a portion of the ring 290 of the C1 vertebra 292. More specifically, the ring engaging portion 348 has an arcuate profile such that the ring engaging portion 348 substantially conforms to the contour of the ring 290 of the C1 vertebra 292. The ring engaging portion 348 has a width such that a plurality of holes 350 are formed in the ring engaging portion 348 in such a way that at least two holes are positionable over the posterior side of the ring 290 of the C1 vertebra 292. The holes 350 may be threaded or non-threaded similar to the holes 56 and 76 discussed above to receive an attachment member, such as attachment members 34.

A first lamina engaging portion 352 extends from the second end 346 of the spacer portion 342, and a second lamina engaging portion 354 extends from the second end 346 of the spacer portion 342. The first and second lamina engaging portions 352 and 354 extend from the spacing portion 342 as to define a notch 356 for receiving the spinous process 320 of the C2 vertebra. Each of the first and the second lamina engaging portions 352 and 354 has a flatter profile than the ring engaging portion 348 so that the lamina engaging portions 352 and 354 substantially conform to the contour of the respective laminae 294 of the C2 vertebra 296. The lamina engaging portions 352 and 354 each has a width such that a plurality of holes 358 are formed in the lamina engaging portions 352 and 354 so that at least two holes are positionable over each of the lamina 294 of the C2 vertebra 296. The holes 358 may be threaded or non-threaded similar to the holes 56 and 76 discussed above to receive an attachment member, such as attachment members 34.

Figure 34A:
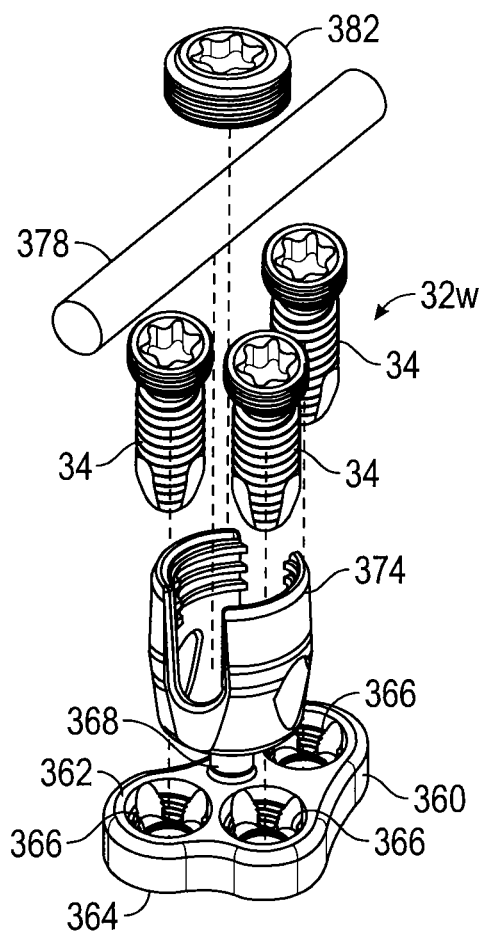
FIG. 34A is an exploded, perspective view of another embodiment of a bone plate constructed in accordance the inventive concepts disclosed herein.
Figure 34B:
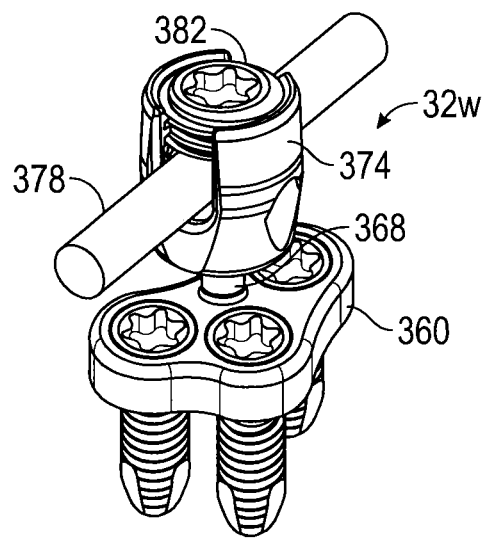
FIG. 34B is a perspective view of the bone plate of FIG. 34A.
Figure 34C:
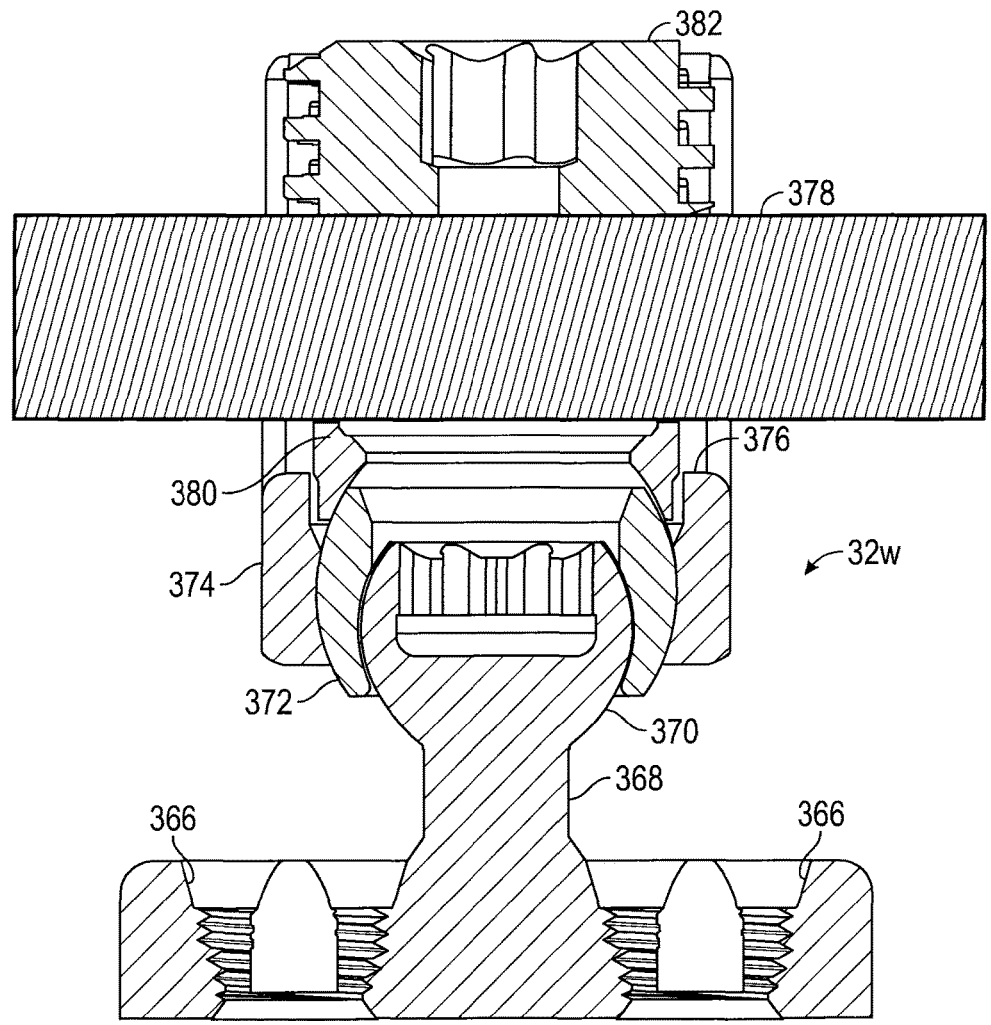
FIG. 34C is a sectional view of the bone plate of FIG. 34B.

Referring now to FIGS. 34A-34C, shown in another embodiment of a bone plate 32w constructed in accordance with the inventive concepts disclosed herein. The bone plate 32w includes a plate portion 360, having an upper surface 362, a lower surface 364, and a plurality of holes 366 extending through the plate portion 360 from the upper surface 362 to the lower surface 364. The plate portion 360 is configured to extend along the posterior side of at least one vertebra adjacent a lateral mass or lamina of the vertebrae and the holes 366 are spaced such that a plurality of holes is positionable over the vertebra to define a plurality of fixation points to the vertebra.

Figure 35A:
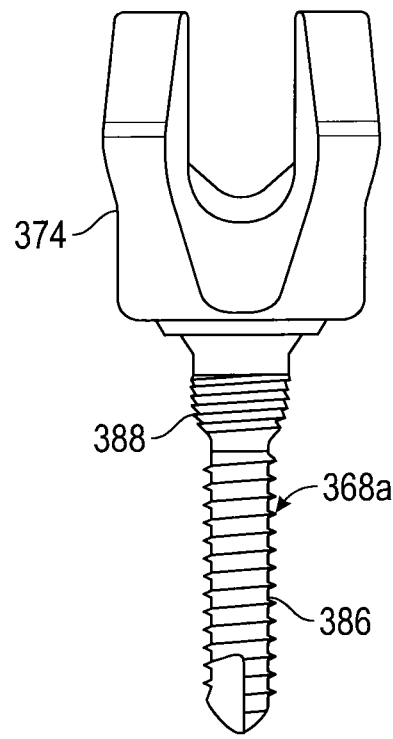
FIG. 35A is an elevational view of an embodiment of a post.
Figure 35B:
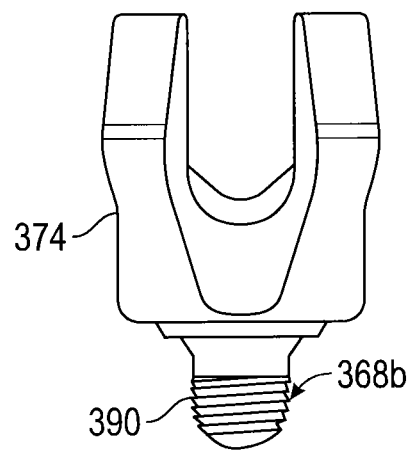
FIG. 35B is an elevational view of another embodiment of a post.

The bone plate 32w further has a post 368 extending from the upper surface 362 of the plate portion 360. The post 368 has an enlarged spherical head portion 370 which is received within a bushing 372 so that the post 368 can poly-axial rotate with respect to the bushing 372. The bushing 372 is positioned an inner spherical cavity formed in a rod receiving head 374. Alternatively, the post 368 may be formed integral with the rod receiving head 374 to form a monolithic structure. Also, as illustrated in FIGS. 35A and 35B, the post may be formed has a separate structure which is adapted to be connected to the plate portion 362 or one of the other bone plates described herein. In one version, a post 368a (FIG. 35A) may include a threaded shaft 386 and a spherical head 388 with variable angle locking threads so that the post 368a is connectable to a bone plate and insertable into bone. In another version, a post 368b (FIG. 35B) may include only a spherical head 390 with variable angle locking threads so that the post 368b is only intended to be connected to a bone plate without providing fixation to bone.

Returning to FIGS. 34A-34C, the rod receiving head 374 has a central passage 376 in which an elongated rod 378 may be seated so as to transversely extend through the central passage 376. The rod 378 may be seated in a saddle 380 positioned about the bushing 372 and secured in the rod receiving head 372 with a threaded locking cap 382 that is threaded to the rod receiving head 374 to lock the rod 378 in place.

Exemplary embodiments of polyaxial screws include those described in International Patent Application No. PCT/US2008/070670, filed on Jul. 21, 2008, entitled "Polyaxial Bone Fixation Element," International Patent Application No. PCT/US2006/015692, filed on Apr. 25, 2006, entitled "Bone Anchor with Locking Cap and Method of Spinal Fixation," and International Patent Application No. PCT/CH1997/00236, filed on Jun. 16, 1997, entitled "Device for Connecting a Longitudinal Support with a Pedicle Screw," the contents of which are hereby incorporated by reference in their entirety. It should be understood, however, that the bone plate 32u is not intended to be limited to any particular type of locking cap or polyaxial screw configuration.

The bone plates described above may be constructed of any suitable biocompatible material which has the structural strength and durability to withstand the cyclical loading associated with long term fixation to the spine. Materials which would be suitable for such applications include, but are not limited to, titanium, titanium alloys (e.g., TAN), steel alloys such as stainless steel, tantalum, polymers such as PEEK, reinforced plastics, allograft bone, and other materials that would be suitable in alternative embodiments, such as composites. When the bone plates are constructed of a polymeric material, the attachment members may be constructed of a like material whereby the attachments members may be secured to the bone plate after insertion by welding. The bone plates can further include one or more bone growth or fusion-promoting elements, such as bone, bone morphogenetic protein (BMP), demineralized bone matrix (DBM), LIM mineralization proteins (LMP), osteogenic pastes, and so forth. It is understood that such fusion-promoting elements are well known by those of ordinary skill in the art.

Although bone plates and the other components of the posterior vertebral plating system have been described herein, it should be understood that the bone plates may include other features as well. For example, the bone plates may include instrument holding features on the outer surface or in the outer edge for facilitating grasping or stabilizing of the bone plates with instruments, such as forceps. Any of the bone plates described herein may be provided with ribs along the upper surface, the edges, or the bottom surface to strength and/or stiffen the bone plates. The bone plates may be foldable or hinged for MIS (minimally-invasive spine surgery) access. The bone plates may be configured to so that one bone plate portion can translate relative to another bone plate portion along a longitudinal axis so that the length of the bone plate may be customized. The bone plates may be made of a mesh material to enable bone plates to be formed of a desired stiffness and without pre-formed holes while still providing the ability to attach the bone plates to selected vertebrae at multiple, selected points per vertebra. The bone plates could be stackable to allow the user to determine the stiffness and strength required for a specific patient.

A variety of kits can be provided that contain any one or more components of any of the posterior vertebral plating system described herein. The components of the kits may be configured the same or differently. For example, within a single kit, bone plates may be provided that have different lengths, different radii of curvature, hole numbers and configurations, differing cross sectional geometries of holes, and so on, depending for example on the type of procedure being performed by a surgeon, or on the particular anatomies of individual patients. The kits may also be configured differently with respect to which components of the system are included in the kits. For example, a kit for fixation of vertebrae via their lateral masses may include plates of different lengths, widths, curvature, contours, hole numbers and patterns, hole angles, hole shapes, and hole types (i.e., for receiving locking or non-locking, variable or non-variable screws).

From the above description, it is clear that the inventive concepts disclosed and claimed herein are well adapted to carry out the objects and to attain the advantages mentioned herein, as well as those inherent in the inventive concepts. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. A posterior vertebral plating system, comprising:
  a plate having an upper surface, a lower surface, and a plurality of holes extending through the plate from the upper surface to the lower surface, the plate being configured to extend along the posterior side of at least two vertebrae adjacent at least one lateral mass of each of the vertebra and the holes being spaced in such a way that a first plurality of holes is positionable over the lateral mass of a first vertebra to define a plurality of fixation points to the first vertebra and a second plurality of holes is positionable over the lateral mass of a second vertebra to define a plurality of fixation points to the second vertebra, and
  a plurality of attachment members insertable through the holes of the plate and into the lateral mass of a corresponding vertebra to fix the plate to the vertebra,
  in which the plate has a first node portion that includes a node protruding laterally relative to a longitudinal direction of the plate and a second node portion that includes a node protruding laterally relative to the longitudinal direction of the plate and that is connected to the first node portion by a recess, the first plurality of holes being located on the first node portion and the second plurality of holes being located on the second node portion,
  in which the holes are arranged in at least two longitudinal rows of holes, the holes of one longitudinal row of holes being staggered relative to the holes of the other longitudinal row of holes, each of the first plurality of holes and the second plurality of holes including one node hole that is located on the node and belongs to the one longitudinal row of holes and two bottom holes that belong to the other longitudinal row of holes, the one node hole and the two bottom holes being arranged in a triangular pattern, and the spacing between each of the one node hole and the two bottom holes being equal, and
  in which the spacing between adjacent bottom holes of the first plurality of holes and the second plurality of holes is greater than the spacing between the node hole and the bottom holes of the first plurality of holes and the spacing between the node hole and the bottom holes of the second plurality of holes.

2. The posterior vertebral plating system of claim 1, in which each of the holes has an axis, in which the holes have a plurality of columns of threads spaced apart to define a plurality of non-threaded recesses, and in which at least one of the columns of threads of one of the holes of a pair of laterally adjacent holes intersects a line extending between the axes of the holes of the pair of laterally adjacent holes.

3. The posterior vertebral plating system of claim 2, in which at least one of the columns of threads of each of the holes of a pair of laterally adjacent holes intersects a line extending between the axes of the holes of the pair of laterally adjacent holes.

4. The posterior vertebral plating system of claim 1, in which the holes have a plurality of columns of threads spaced apart to define a plurality of non-threaded recesses, and in which the plate further includes a flange extending between adjacent columns of threads of at least one hole near the lower surface of the plate in such a way that the flange impedes the attachment members from being driven entirely through the hole.

5. The posterior vertebral plating system of claim 1, in which the holes have a plurality of columns of threads spaced apart to define a plurality of non-threaded recesses between adjacent columns of threads, and in which the plate further includes a flange extending between adjacent columns of threads near the lower surface of the plate in such a way that the flange impedes the attachment members from being driven entirely through the hole.

6. The posterior vertebral plating system of claim 1, in which the plate has a perimeter edge extending between the upper surface and the lower surface, and in which the perimeter edge is configured to substantially conform to the contour of the holes of the plate.

7. The posterior vertebral plating system of claim 1, in which the plate has a longitudinal edge, and in which the plate has a rod portion formed along the longitudinal edge of the plate.

8. The posterior vertebral plating system of claim 7, further comprising a lamina connector having a plate portion and a rod engaging portion, the plate portion positionable over a lamina of a vertebra when the rod engaging portion is engaged with the rod portion of the plate and the plate is connected to the vertebrae.

9. The posterior vertebral plating system of claim 7, further comprising a crosslinking connector including a rod portion and a rod engaging portion formed on each of the rod portion, the rod extendable from one side of a vertebra to an opposing side of the vertebra when one of the rod engaging portions is engaged with the rod portion of the plate and the plate is connected to the vertebra.

10. The posterior vertebral plating system of claim 7, in which the rod portion extends beyond at least one end of the plate.

11. The posterior vertebral plating system of claim 1 in which the plate has an outer longitudinal edge, and in which the plate further has a bone graft ridge extending upwardly and outwardly from the outer longitudinal edge of the plate so as define a pocket beneath the bone graft ridge in which biologic material may be packed.

12. The posterior vertebral plating system of claim 1, in which the plate has an inner longitudinal edge and an outer longitudinal edge, and in which the plate has a pair of flanges extending downwardly from lower surface thereof along the inner longitudinal edge and the outer longitudinal edge so as to define a pocket in which biologic material may be packed.

13. The posterior vertebral plating system of claim 1, in which the plate includes a first plate portion and a second plate portion, and in which the first plate portion is pivotally connected to the second plate portion.

14. The posterior vertebral plating system of claim 13, in which the first plate portion is longitudinally aligned with the second plate portion.

15. The posterior vertebral plating system of claim 1, in which the plate has the greatest width at a location of the node and has the smallest width at a location of the recess.

16. A posterior vertebral plating system, comprising:
a plate having an upper surface, a lower surface, and a plurality of holes extending through the plate from the upper surface to the lower surface, the plate being configured to extend along the posterior side of at least two vertebrae adjacent at least one lateral mass of each of the vertebra and the holes being spaced in such a way that a first plurality of holes is positionable over the lateral mass of a first vertebra to define a plurality of fixation points to the first vertebra and a second plurality of holes is positionable over the lateral mass of a second vertebra to define a plurality of fixation points to the second vertebra, and
a plurality of attachment members insertable through the holes of the plate and into the lateral mass of a corresponding vertebra to fix the plate to the vertebra,
in which the plate has a first node portion that includes a node protruding laterally relative to a longitudinal direction of the plate and a second node portion that includes a node protruding laterally relative to the longitudinal direction of the plate and that is connected to the first node portion by a recess, the first plurality of holes being located on the first node portion and the second plurality of holes being located on the second node portion,
in which the holes are arranged in at least two longitudinal rows of holes, the holes of one longitudinal row of holes being staggered relative to the holes of the other longitudinal row of holes, each of the first plurality of holes and the second plurality of holes including one node hole that is located on the node and belongs to the one longitudinal row of holes and two bottom holes that belong to the other longitudinal row of holes, the one node hole and the two bottom holes being arranged in a triangular pattern, and the spacing between each of the one node hole and the two bottom holes being equal, and
in which the plate has the greatest width at a location of the node and has the smallest width at a location of the recess.

* * * * *